(12) United States Patent
Dye

(10) Patent No.: US 9,878,125 B2
(45) Date of Patent: Jan. 30, 2018

(54) INTERMITTENT URINARY CATHETER

(71) Applicant: Philip J. Dye, Akron, OH (US)

(72) Inventor: Philip J. Dye, Akron, OH (US)

(73) Assignee: ZCATH LLC, Cuyahoga Falls, OH (US)

(*) Notice: Subject to any disclaimer, the term of this patent is extended or adjusted under 35 U.S.C. 154(b) by 0 days.

(21) Appl. No.: 15/287,781

(22) Filed: Oct. 7, 2016

(65) Prior Publication Data
US 2017/0021130 A1    Jan. 26, 2017

Related U.S. Application Data

(63) Continuation-in-part of application No. 14/723,883, filed on May 28, 2015, now Pat. No. 9,486,603, (Continued)

(51) Int. Cl.
*A61M 25/00* (2006.01)
*A61M 25/04* (2006.01)

(52) U.S. Cl.
CPC .... *A61M 25/0023* (2013.01); *A61M 25/0017* (2013.01); *A61M 25/04* (2013.01); *A61M 25/0068* (2013.01); *A61M 2025/006* (2013.01); *A61M 2210/1085* (2013.01); *A61M 2210/1089* (2013.01)

(58) Field of Classification Search
CPC .......... A61M 25/0017; A61M 25/0023; A61M 25/04; A61M 2025/006; A61M 2210/1085; A61M 2210/1089; A61M 25/0068; A61M 2025/0059
See application file for complete search history.

(56) References Cited

U.S. PATENT DOCUMENTS

| 1,596,754 A | 8/1926 | Moschelle |
| 1,638,532 A | 8/1927 | Kallmeyer |

(Continued)

FOREIGN PATENT DOCUMENTS

| DE | 3312672 | 10/1984 |
| EP | 0384476 | 8/1990 |

(Continued)

OTHER PUBLICATIONS

"Wave-Rib™ Duct"—www.gatesupply.com (http://www.gatelsupply.com/index.cfm/feature/69/wave-rib-conduit-a-d-technologies.cfm), Accessed Jun. 13, 2013.

(Continued)

*Primary Examiner* — Adam Marcetich
(74) *Attorney, Agent, or Firm* — Howard L. Wernow; Sand & Sebolt

(57) ABSTRACT

A catheter has an entrance opening defined by the first end of a catheter body and non-circular inner surface in cross section. The entrance opening intersects a longitudinal axis extending longitudinally through the center of a lumen adapted to drain urine from a bladder. The non-circular inner surface can have dimples, channels, or grooves, all of which decrease frictional fluid forces against the inner surface as the urine drains. The catheter is free of any eyelets formed in the side wall of the catheter body. The catheter further includes a plurality of distinct longitudinally extending convex outer surfaces and may have an enlarged head.

21 Claims, 27 Drawing Sheets

Related U.S. Application Data which is a continuation-in-part of application No. 13/922,667, filed on Jun. 20, 2013, now Pat. No. 9,289,575.

(56) References Cited

U.S. PATENT DOCUMENTS

| | | | |
|---|---|---|---|
| 3,608,555 A | 9/1971 | Greyson | |
| 3,630,206 A | 12/1971 | Gingold | |
| 3,807,408 A * | 4/1974 | Summers | A61M 25/0017 604/104 |
| 3,815,608 A | 6/1974 | Spinosa | |
| 3,945,385 A | 3/1976 | Sackner | |
| 3,948,273 A * | 4/1976 | Sanders | A61M 16/0463 128/207.15 |
| 4,307,723 A | 12/1981 | Finney | |
| 4,531,943 A | 7/1985 | Van Tassel et al. | |
| 4,601,713 A | 7/1986 | Fuqua | |
| 4,717,379 A | 1/1988 | Ekholmer | |
| 4,808,154 A * | 2/1989 | Freeman | A61F 9/00745 604/22 |
| 4,840,623 A * | 6/1989 | Quackenbush | A61M 25/0021 138/108 |
| 4,863,441 A * | 9/1989 | Lindsay | A61M 25/00 604/264 |
| 4,955,862 A | 9/1990 | Sepetka | |
| 4,981,477 A * | 1/1991 | Schon | A61M 1/008 604/264 |
| 5,116,327 A | 5/1992 | Seder | |
| 5,244,619 A | 9/1993 | Burnham | |
| 5,401,257 A | 3/1995 | Chevalier et al. | |
| 5,558,737 A | 9/1996 | Brown et al. | |
| 5,573,521 A | 11/1996 | McFarlane | |
| 5,578,006 A | 11/1996 | Schon | |
| 5,593,394 A * | 1/1997 | Kanesaka | A61M 25/0023 604/524 |
| 5,643,230 A | 7/1997 | Linder | |
| 5,700,252 A | 12/1997 | Klingenstein | |
| 5,762,631 A | 6/1998 | Klein | |
| 5,788,680 A | 8/1998 | Linder | |
| 5,797,882 A * | 8/1998 | Purdy | A61M 25/0023 604/164.09 |
| 5,836,926 A | 11/1998 | Peterson et al. | |
| 5,860,963 A | 1/1999 | Azam et al. | |
| 5,879,342 A | 3/1999 | Kelley | |
| 5,885,508 A | 3/1999 | Ishida | |
| 5,891,111 A | 4/1999 | Ismael | |
| 5,896,896 A | 4/1999 | Rojey | |
| 5,938,587 A | 8/1999 | Taylor et al. | |
| 5,984,904 A * | 11/1999 | Steen | A61F 9/00745 604/22 |
| 6,007,521 A | 12/1999 | Bidwell et al. | |
| 6,080,141 A * | 6/2000 | Castro | A61M 25/0668 604/164.01 |
| 6,491,670 B1 | 12/2002 | Toth | |
| 6,585,718 B2 | 7/2003 | Hayzelden et al. | |
| 8,323,241 B2 | 12/2012 | Salahieh | |
| 9,289,575 B2 | 3/2016 | Dye | |
| 2002/0173816 A1 | 11/2002 | Hung | |
| 2002/0183781 A1 | 12/2002 | Casey | |
| 2004/0167595 A1 * | 8/2004 | Tuominen | A61M 25/0009 607/122 |
| 2004/0267211 A1 | 12/2004 | Akahoshi | |
| 2005/0010169 A1 | 1/2005 | Kuhlein et al. | |
| 2005/0021001 A1 * | 1/2005 | Chong | A61L 29/085 604/523 |
| 2005/0199521 A1 | 9/2005 | Givens | |
| 2005/0234426 A1 | 10/2005 | Weber et al. | |
| 2005/0277942 A1 * | 12/2005 | Kullas | A61F 2/0063 606/99 |
| 2006/0116661 A1 | 6/2006 | Tanghoej | |
| 2006/0142736 A1 | 6/2006 | Hissink et al. | |
| 2006/0161135 A1 | 7/2006 | VanDerWoude | |
| 2006/0211952 A1 | 9/2006 | Kennedy, II | |
| 2006/0229574 A1 * | 10/2006 | Sherman | A61M 25/0043 604/264 |
| 2006/0253104 A1 | 11/2006 | Pandey et al. | |
| 2006/0264905 A1 | 11/2006 | Eskridge et al. | |
| 2007/0149950 A1 | 6/2007 | Perkins et al. | |
| 2007/0260199 A1 | 11/2007 | Rockley | |
| 2008/0045885 A1 | 2/2008 | Callahan et al. | |
| 2008/0065002 A1 | 3/2008 | Lobl et al. | |
| 2008/0125699 A1 | 5/2008 | Davis | |
| 2008/0154206 A1 | 6/2008 | Guo | |
| 2008/0228154 A1 | 9/2008 | Williams et al. | |
| 2009/0124988 A1 | 5/2009 | Coulthard | |
| 2009/0131751 A1 | 5/2009 | Spivey | |
| 2009/0227937 A1 | 9/2009 | Akahoshi | |
| 2009/0234227 A1 | 9/2009 | Punga | |
| 2010/0130939 A1 * | 5/2010 | Voss | A61M 25/0009 604/167.03 |
| 2010/0198160 A1 | 8/2010 | Voss | |
| 2010/0324540 A1 | 12/2010 | Paulen et al. | |
| 2011/0172642 A1 | 7/2011 | Lareau | |
| 2012/0041419 A1 | 2/2012 | Blanchard et al. | |
| 2012/0239004 A1 | 9/2012 | Wong | |
| 2013/0110086 A1 | 5/2013 | Bhagchandani et al. | |
| 2013/0184659 A1 | 7/2013 | Byrnes et al. | |
| 2013/0247904 A1 | 9/2013 | Porat | |
| 2013/0253479 A1 | 9/2013 | Su | |
| 2015/0088072 A1 * | 3/2015 | Voss | A61M 25/0009 604/164.01 |

FOREIGN PATENT DOCUMENTS

| | | |
|---|---|---|
| EP | 1818071 | 8/2007 |
| EP | 2826515 | 1/2015 |
| FR | 2940914 | 7/2010 |
| WO | 03/028798 | 4/2003 |

OTHER PUBLICATIONS

PVC—Ultra Corr™ / Ultra Rib™—www.jmeagle.com (http://www.jmeagle.com/pdfs/2008%20Brochures/Ultra%20Corr%20Ultra%20Rib_web.pdf), Accessed Jun. 13, 2013.

Raul Ordorica, M.D. et al., "How Foley Catheter Design Flaws May Lead to CAUTIs: The Problem and a Potential Solution", Aug. 2015, www.poiesismedical.com/wp-content/uploads/2012/03/White-Paper-Final.pdf, accessed on Oct. 10, 2016.

* cited by examiner

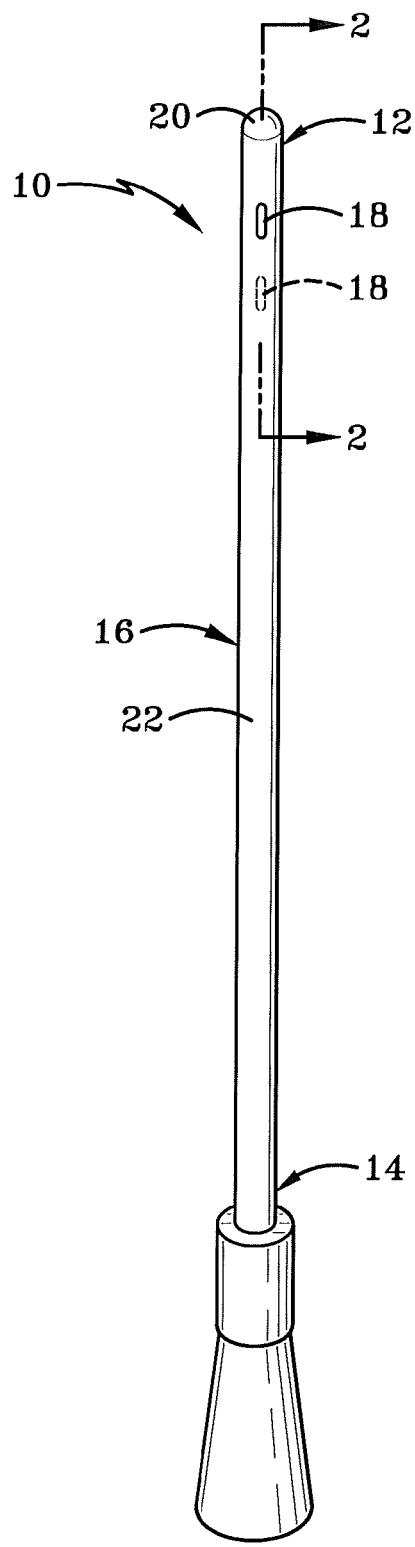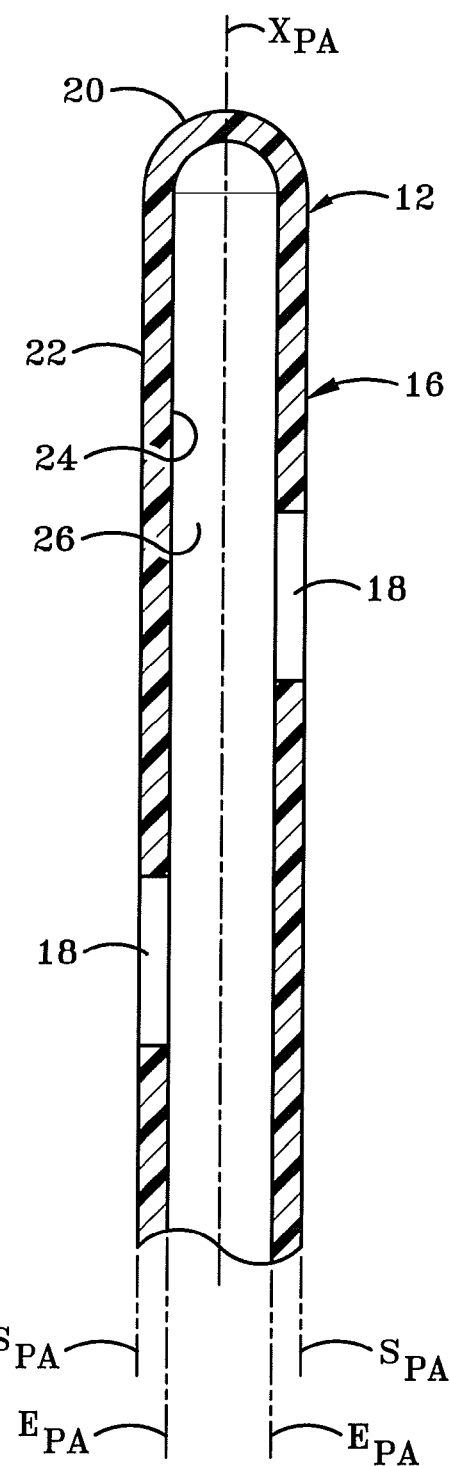
FIG.1
PRIOR ART
FIG.2
PRIOR ART

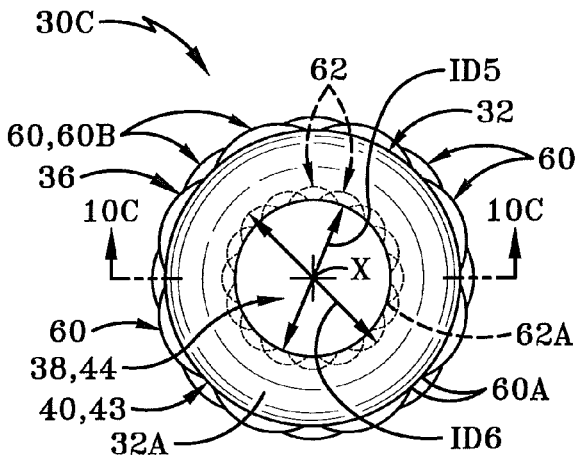
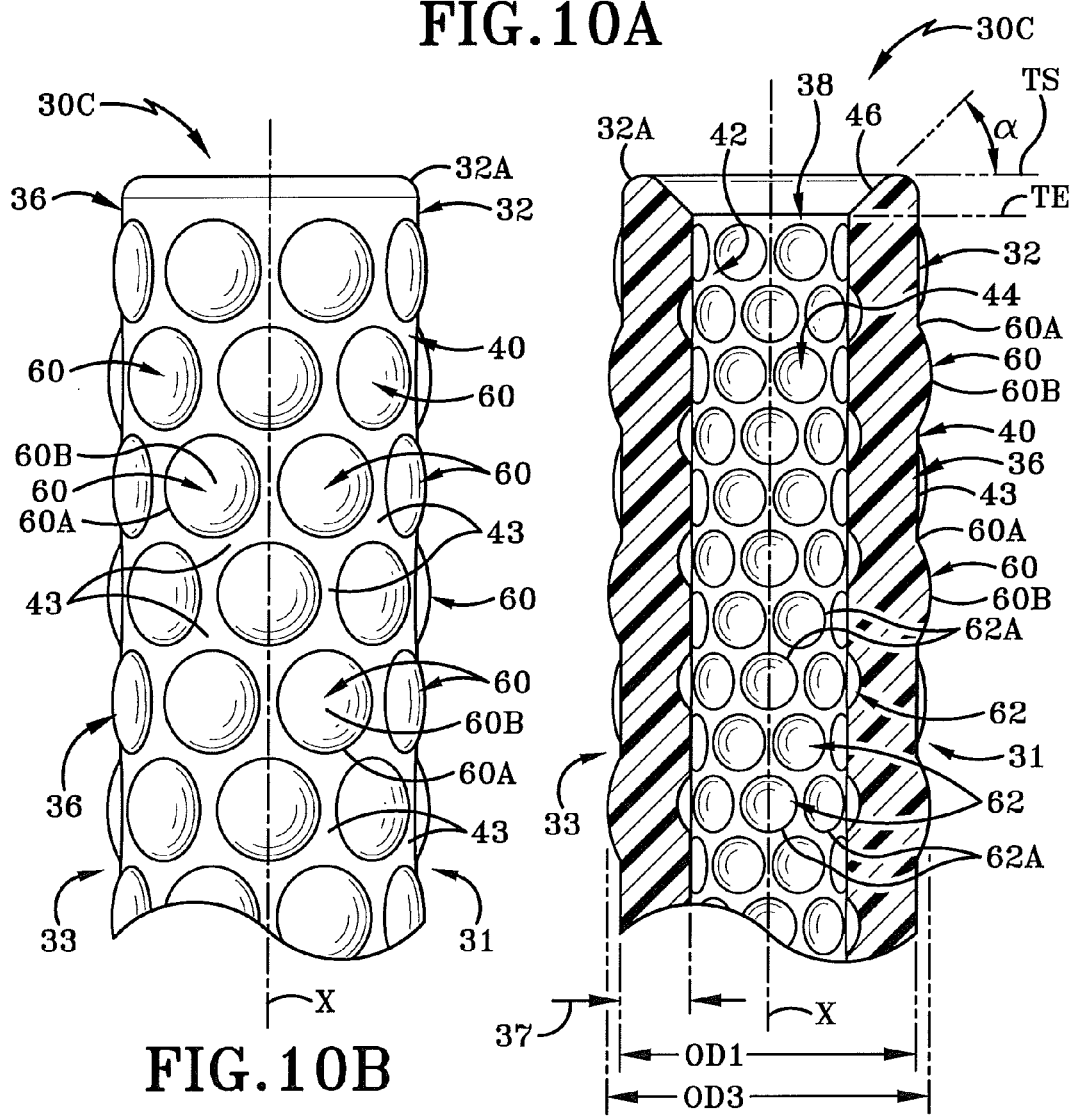
FIG.10A
FIG.10B
FIG.10C

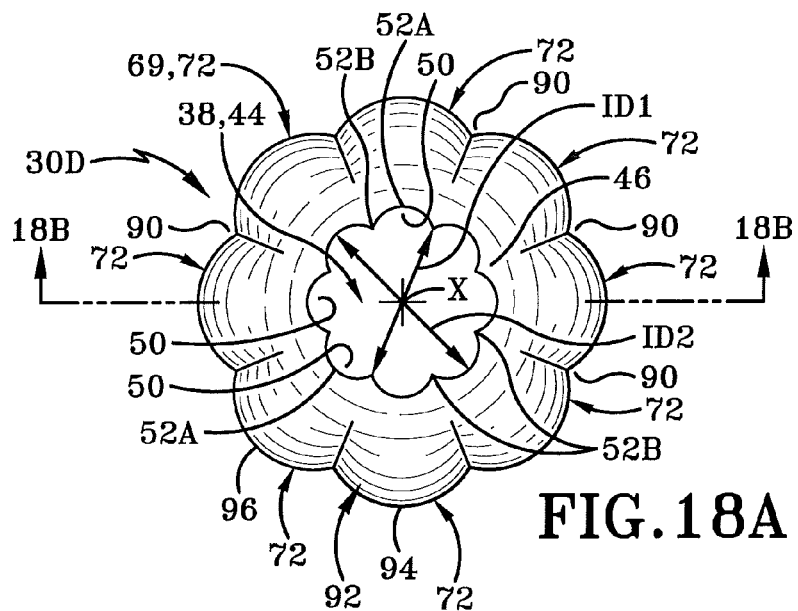
FIG.18A
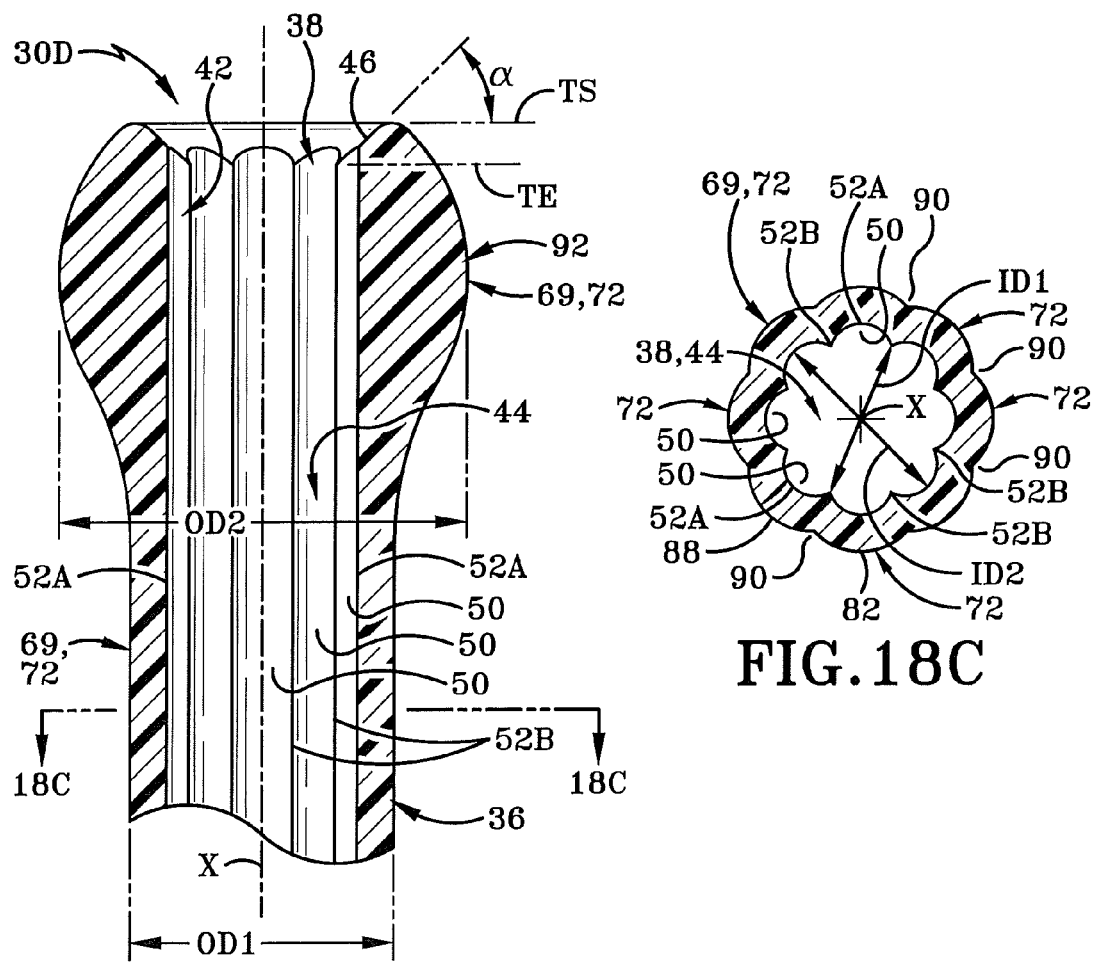
FIG.18B
FIG.18C

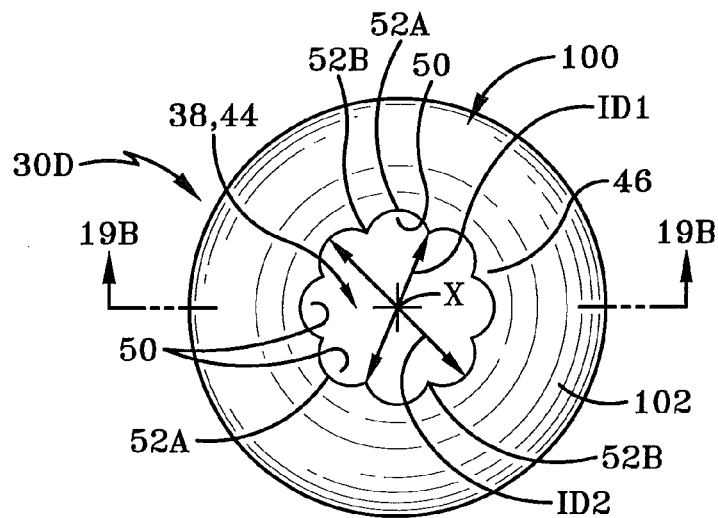
FIG.19A
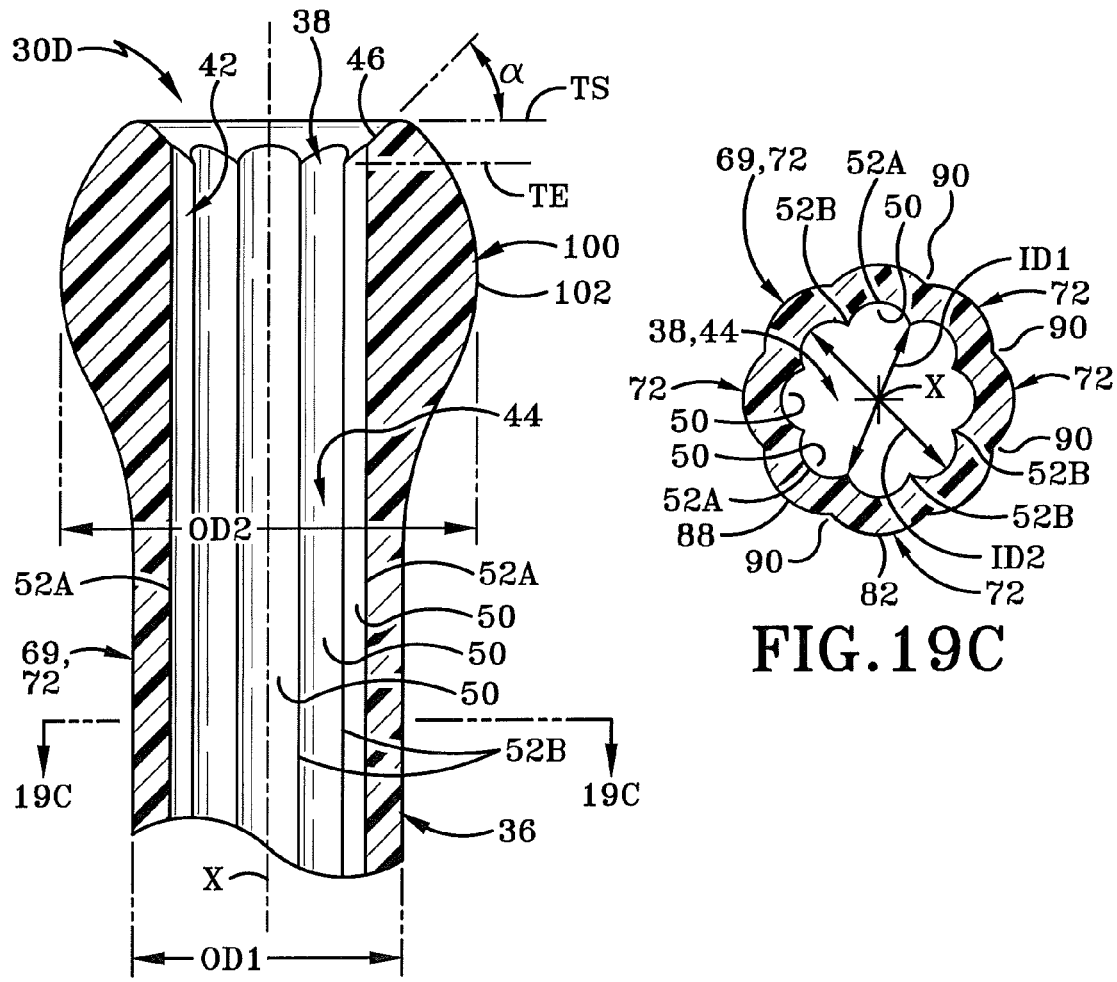
FIG.19C
FIG.19B

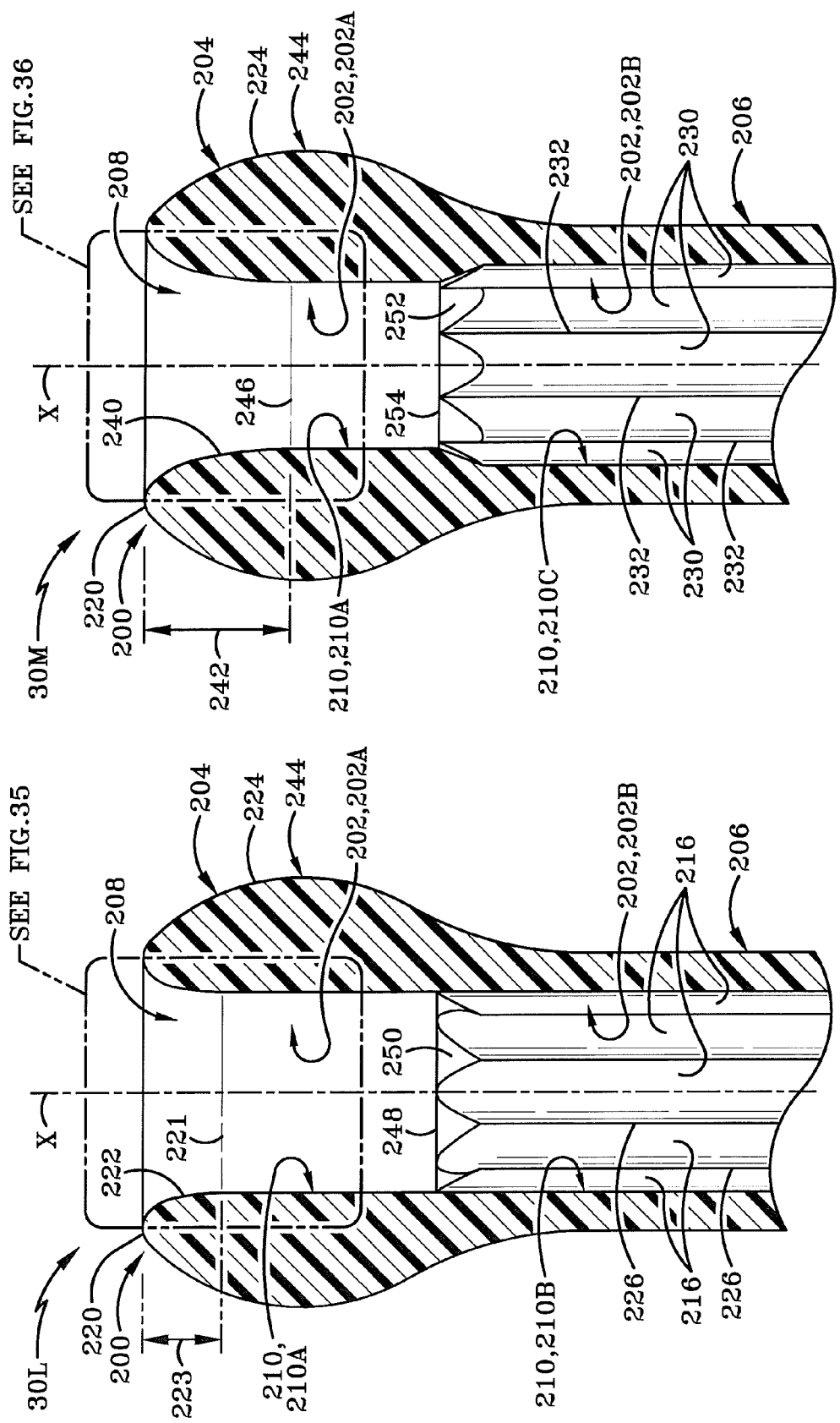

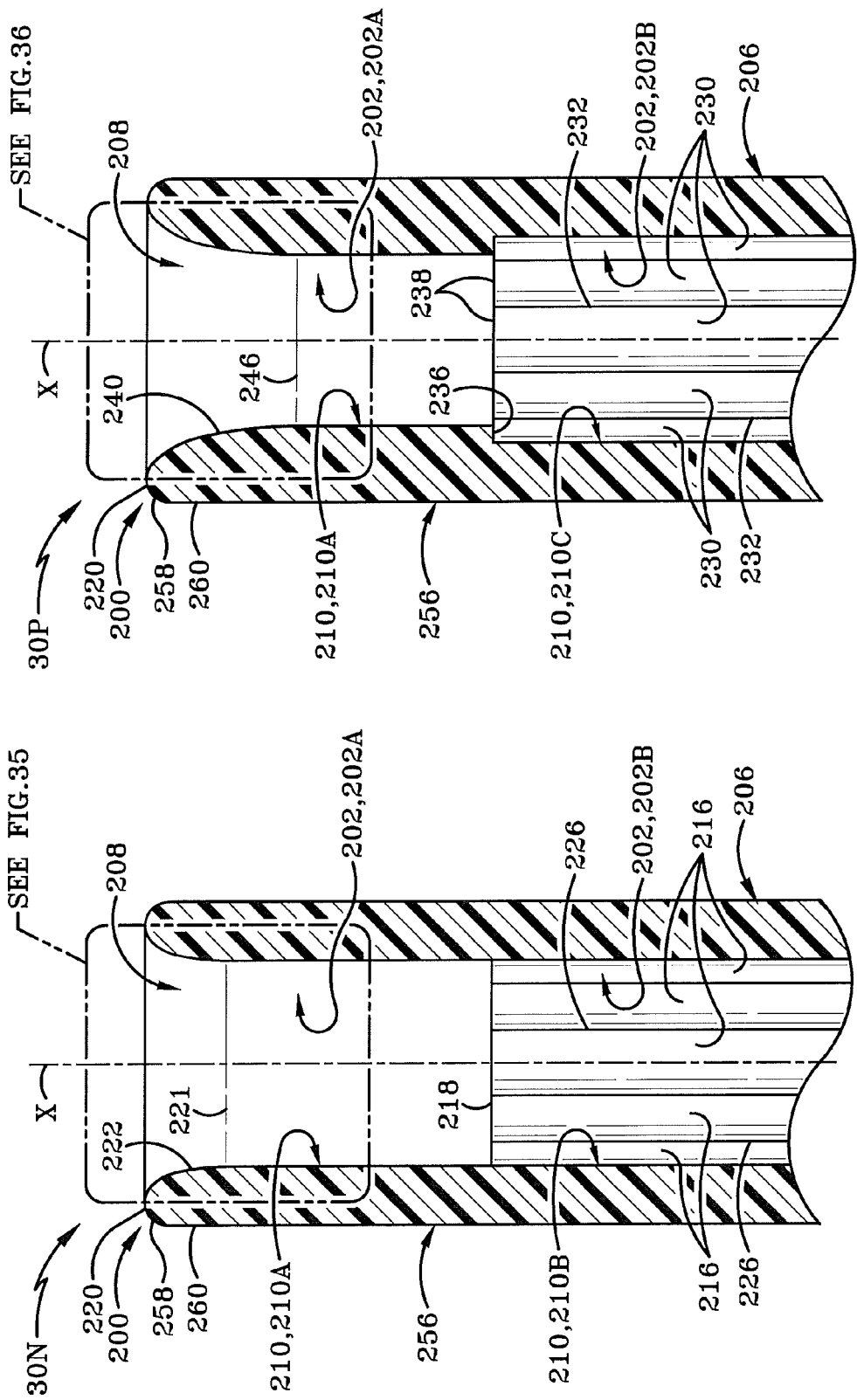

INTERMITTENT URINARY CATHETER

CROSS REFERENCE TO RELATED APPLICATION

This application is a continuation-in-part application that claims priority from pending prior U.S. patent application Ser. No. 14/723,883, filed on May 28, 2015, which is a continuation-in-part application of U.S. patent application Ser. No. 13/922,667, now U.S. Pat. No. 9,289,575, filed Jun. 20, 2013; the entire disclosure of each of the foregoing is incorporated herein by reference as if fully rewritten.

BACKGROUND

Technical Field

The present disclosure relates generally to a medical device. More particularly, the present disclosure pertains to a catheter for draining urine from a bladder. Specifically, the present disclosure provides a catheter having an opening at a first end and a sidewall that is free of eyelets, and wherein the catheter provides an atraumatic insertion tip compared to conventional catheters.

Background Information

Urinary catheters are extremely useful medical devices. Generally, a urinary catheter is inserted into the urethral canal of a patient to drain urine from the bladder when they need assistance urinating. Current catheter designs have a catheter body sidewall with two to four eyelets or intake apertures formed in the catheter body sidewall at one end and often a hemispheric tip enclosing one end to facilitate insertion into a urethral canal. The eyelets are known to those in the urology field to cause trauma to the urethra. During insertion, the edges of the eyelets can cut the urethra wall, similar to the way a box grater or box shredder cuts a piece of cheese, often leading to serious infections requiring extreme medical attention.

Improvements on this basic design have come and gone through the years, such as smoother and polished eyelet designs to decrease the risk of infection often attributed to insertion agitation. Yet, these catheters still have drawbacks. Slow drainage time is often a problem because the eyelet formed in the catheter body sidewall causes turbulent fluid forces within the catheter. Further, friction forces created by the urine flow contacting the inner surface of the catheter decreases the fluid flow or drainage rate. The eyelets also have a likelihood of becoming clogged with mucus or debris contained in the bladder, or clogged with lubricant used during the insertion process.

SUMMARY

Inasmuch as drawbacks continue to exist with respect to currently known intermittent urinary catheters as detailed by way of background above, there is a need in the art for an improved catheter that addresses some or all of the drawbacks of the currently known designs. The present disclosure addresses some of these issues.

In one aspect, an embodiment may provide an improved catheter that has a single entrance opening located at the first end instead of the two to four eyelets formed in the sidewall of conventional catheters. Further, the improved catheter defines an atraumatic insertion tip relative to a conventional catheter having two eyelets. The improved catheter is structurally strong enough to allow the entrance opening to be introduced first into the urethral canal without the need for a tip.

In one aspect, an embodiment may provide a catheter comprising: a generally cannular body having an annular sidewall with first and second ends that therebetween define an longitudinal axis, said first end adapted to be inserted into a urethral canal; said body having an outer surface spaced apart from an inner surface; a lumen defined by the inner surface adapted to drain the fluid from a bladder; and a single entrance opening defined in the first end wherein a plane of the opening intersects the longitudinal axis.

In another aspect, another embodiment may provide a catheter comprising: a body having an annular sidewall extending along a longitudinal axis between first and second ends, said body having an outer surface spaced apart from an inner surface; a lumen defined by the body extending longitudinally from first end to second end adapted to drain fluid from a hollow organ; and an entrance opening formed in the first end in longitudinal alignment with the lumen and including an entrance opening plane intersecting the axis in a generally perpendicular manner.

In another aspect, another embodiment may provide a catheter comprising: a catheter having first and second ends with a generally cannular body extending therebetween along a longitudinal axis; said body having an outer surface spaced apart from an inner surface; said inner surface having a non-circular cross section when viewed from above; a lumen defined by the non-circular inner surface adapted to drain fluid from a hollow organ; and an entrance opening formed in the first end in fluid communication with the lumen.

In yet another aspect, an embodiment may provide a method for draining a human bladder comprising the steps of: providing a catheter having an annular sidewall with first and second ends that therebetween define a longitudinal axis, and having an entrance opening defined in the first end of the body; wherein a plane of the opening intersects the longitudinal axis; aligning the first end of the catheter body with the entrance to a patient's urethral canal; inserting the first end of the catheter into the urethral canal; moving the catheter through the urethral canal towards the patient's bladder; establishing fluid communication between the catheter and the bladder; causing urine to flow from the bladder through the entrance opening; through a lumen defined in the catheter, where the lumen is longitudinally aligned with the entrance opening; through an aperture defined in the second end of the catheter body, where the aperture is longitudinally aligned with the lumen; and into a drainage tube engaged with the second end of the catheter body; draining a quantity of urine from the bladder; and removing the catheter after the quantity of urine has drained from the bladder.

Still further, an embodiment may provide an intermittent urinary catheter comprising: a generally flexible tubular body member defining a lumen extending centrally along a longitudinal axis from a first end to a second end, said first end adapted to be inserted into a urethral canal of a patient; an outer surface spaced apart from an inner surface of the tubular member, wherein the inner surface defines the lumen adapted to drain the fluid from the patient's bladder; and a plurality of distinct longitudinally extending convex surfaces positioned circumferentially about the longitudinal axis collectively defining the outer surface.

In another aspect, an embodiment may provide an intermittent urinary catheter comprising: a generally flexible tubular body member defining a lumen extending centrally along a longitudinal axis from a first end to a second end, said first end adapted to be inserted into a urethral canal of a patient; an outer surface spaced apart from an inner surface of the tubular member, wherein the inner surface defines the lumen adapted to drain the fluid from the patient's bladder; an entrance opening formed adjacent the first end of the of the tubular body member in fluid communication with the lumen; and an enlarged tip formed adjacent the first end of the tubular body member, the enlarged tip having a diameter greater than that of the tubular body member, said enlarged tip adapted to guide the intermittent urinary catheter through the urethral canal.

In another aspect, an embodiment may provide a catheter comprising: a first end opposite a second end defining a longitudinal axis therebetween; a tubular body extending from the first end to the second end having an outer surface and an inner surface defining a lumen adapted to drain fluid from an organ or organic vessel; a first section of the inner surface proximate the first end that is generally circular in cross section; and a second section of the inner surface that is generally non-circular in cross section. In a further embodiment, there may include a plurality of longitudinal channels formed in the second section extending towards the second end from a first plane orthogonal to the longitudinal axis; wherein the first section is offset opposite the first plane relative to the second section. In a further embodiment, the first plane may be in a range from about 0.1 inches to about 2 inches from the first end of the tubular body. In a further embodiment, there may include a rounded endwall at the first end; an arcuately convex transitional surface narrowing inwardly towards the longitudinal axis; wherein the rounded endwall and the arcuately convex transitional surface define an entrance opening generally orthogonal to the longitudinal axis. In a further embodiment, there may include an enlarged head defining a portion of the outer surface positioned proximate the first end; an arcuately convex transitional wall narrowing inwardly towards the longitudinal axis defining an entrance opening to the lumen. In a further embodiment, there may include an end plane associated with transitional wall where the transitional wall meets the first section of the inner surface; wherein the end plane intersects the enlarged head. In a further embodiment, the end plane may intersect the enlarged head at an apex. In a further embodiment, there may include a plurality of channels defining the second section of the inner surface, wherein the channels are arcuately concave positioned circumferentially around the longitudinal axis. In a further embodiment, the plurality of channels is an odd number of channels, or wherein the number of channels is selected from the group consisting of: five channels, seven channels, or nine channels. In a further embodiment, there may include a plurality of longitudinally extending arcuately convex surfaces collectively defining the outer surfaces of the tubular body. In a further embodiment, there may include, a vertically asymmetric parabolically-shaped transitional wall extending inwardly from the first end to the first section of the inner surface. In a further embodiment, there may include a beveled transition between the first section and the second section of the inner surface. In a further embodiment, there may include a point on the non-circular second section of the inner surface having a radius relative to the longitudinal axis that is different than a radius of the first section of the inner surface.

In another aspect, an embodiment may provide a catheter comprising: a first end opposite a second end defining a longitudinal axis therebetween; a tubular body extending from the first end to the second end having an outer surface and an inner surface defining a lumen adapted to drain fluid from an organ or organic vessel; an enlarged head forming a portion of the outer surface proximate the first end, and the enlarged head having a diameter greater than the tubular body; a rounded endwall at the first end; and an arcuately convex transitional wall narrowing from the rounded end to the inner surface of the tubular body, wherein the rounded endwall and the arcuately convex transitional wall define an opening generally orthogonal to the longitudinal axis. In a further embodiment, the rounded endwall and the arcuately convex transitional wall may be vertically asymmetric. In a further embodiment, the arcuately convex transitional wall may decrease in diameter from the first end towards the second end; and wherein the enlarged head may increase in diameter from the first end towards an apex of maximum diameter and then decreases in diameter from the apex towards the second end. In a further embodiment, there may include a plurality of arcuately convex surfaces collectively defining the outer surface of the tubular body; and a plurality of arcuately concave surfaces collectively defining a portion of the inner surface of the tubular body. In a further embodiment, there may include a first section of the inner surface having a circular cross section; and a second section of the inner surface having a non-circular cross-section defined by the plurality of arcuately concave surfaces. In a further embodiment, there may include a beveled transition wall intermediate the first section and the second section of the inner surface.

BRIEF DESCRIPTION OF THE SEVERAL VIEWS OF THE DRAWINGS

A sample embodiment of the present disclosure, illustrative of the best mode in which Applicant contemplates applying the principles, is set forth in the following description, is shown in the drawings and is particularly and distinctly pointed out and set forth in the appended claims.

FIG. 1 is a perspective view of a PRIOR ART catheter having two eyelets in the catheter's sidewall and a hemispheric tip at a first end of the catheter;

FIG. 2 is a cross section view taken along line 2-2 in FIG. 1 depicting a PRIOR ART catheter having two eyelets in the body sidewall that do not intersect the longitudinal axis and having a smooth inner and outer surface;

FIG. 10A is a top view of the first end of a third embodiment of the catheter depicting a dimpled outer surface and a fourth variation of the lumen having a dimpled inner surface;

FIG. 10B is a side elevation view of the third embodiment of the catheter depicting the convex dimples extending along the outer surface;

FIG. 10C is a cross section view taken along line 10C-10C in FIG. 10A;

FIG. 18A is a top view of the first end of the fourth embodiment catheter having a bulbous head and a plurality of distinct convex surfaces on the outer surface extending over the head;

FIG. 18B is a cross section view taken along line 18B-18B in FIG. 18A;

FIG. 18C is a cross section view take along line 18C-18C in FIG. 18B;

FIG. 19A is a top view of the first end of the fourth embodiment catheter having a bulbous head and a plurality of distinct convex surfaces on the outer surface beginning below the bulbous head and a continuous smooth surface of the head;

FIG. 19B is a cross section view taken along line 19B-19B in FIG. 19A;

FIG. 19C is a cross section view take along line 19C-19C in FIG. 19B;

FIG. 31 is an enlarged cross-section view of the first end of a twelfth embodiment catheter;

FIG. 32 is an enlarged cross-section view of the first end of a thirteenth embodiment catheter;

FIG. 33 is an enlarged cross-section view of the first end of a fourteenth embodiment catheter;

FIG. 34 is an enlarged cross-section view of the first end of a fifteenth embodiment catheter;

Similar numbers refer to similar parts throughout the drawings.

DETAILED DESCRIPTION

Figure 3:
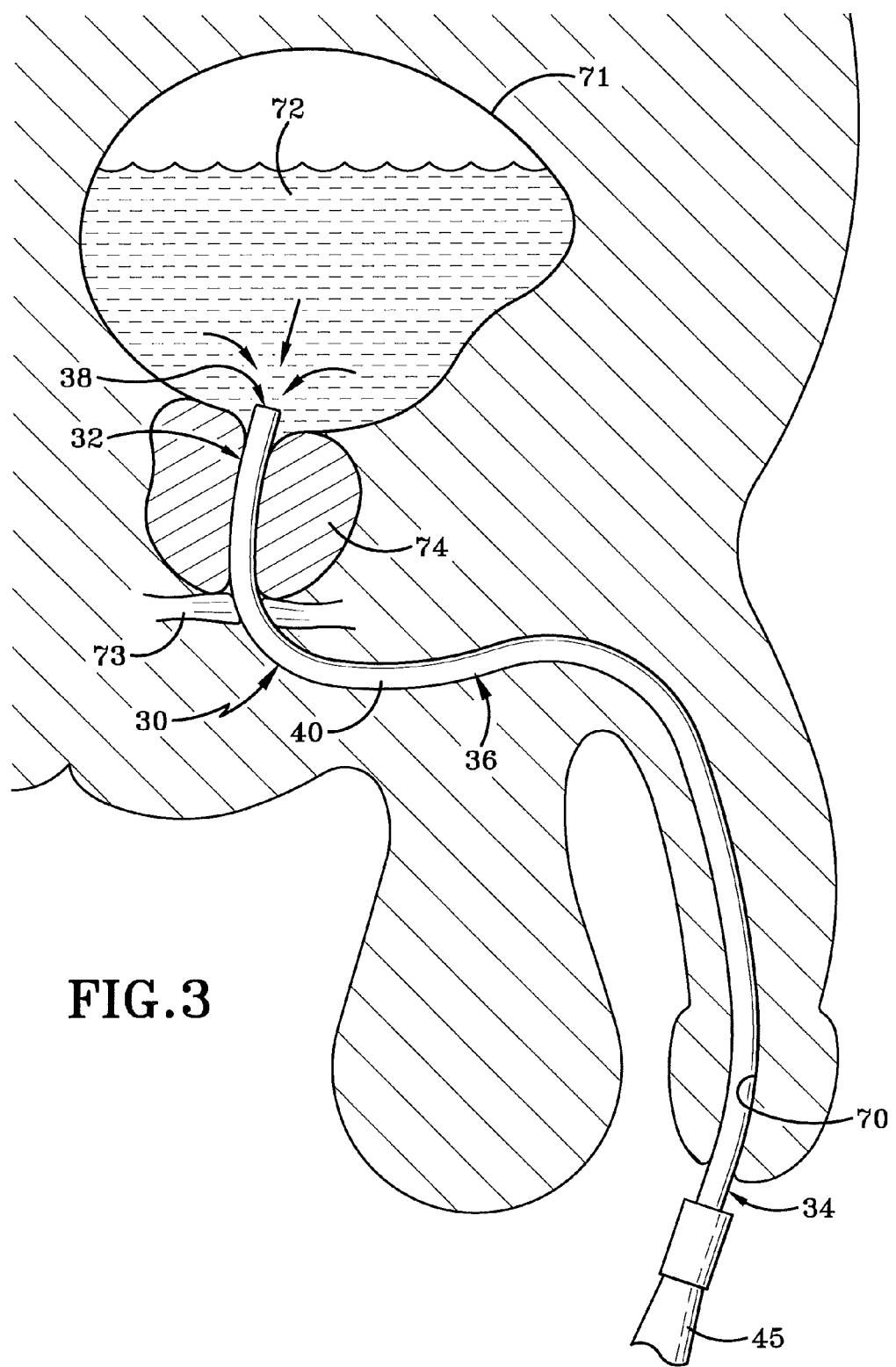
FIG. 3 is a diagrammatic view of the catheter of the present disclosure depicting it in vivo utilization.

With primary reference to FIGS. 1 and 2, a catheter 10 as conventionally known in the PRIOR ART has a first end 12, a second end 14, a catheter body or annular sidewall 16 extending from first end 12 to second end 14, eyelets 18, a first end wall 20 at the first end 12 that forms a tip which is hemispheric in shape and substantially continuous, a sidewall outer surface 22, a sidewall inner surface 24, and a lumen 26 defined by inner surface 24. Catheter body 16 is generally cannular or tubular extending from first end 12 to second end 14 and defining therebetween a longitudinal axis $X_{pa}$. Eyelets 18 are formed in the catheter sidewall extending from a start plane $S_{pa}$ along outer surface 22 to and end plane $E_{pa}$ along inner surface 24 proximate the first end 12. The respective start and end planes, $S_{pa}$, $E_{pa}$, of the eyelets are parallel to longitudinal axis $X_{pa}$. When viewed from a side cross section (FIG. 2) and extrapolated beyond the respective start and end planes, $S_{pa}$, $E_{pa}$, eyelets 18 are at right angles to the longitudinal axis $X_{pa}$. Eyelets 18 are in fluid communication with lumen 16 permitting fluid to drain through catheter 10 and out and exit opening (not shown) defined in the second end 14, which may be configured to fluidly communicate with a drainage tube or system (not shown). End wall 20 intersects longitudinal axis $X_{pa}$ and is substantially solid and continuous. However, there are some known prior art catheters 10 that may contain a small or "pin-hole" opening within end wall 20, wherein this pin-hole opening has a substantially smaller diameter than the lumen 16 diameter. The outer and inner surfaces 22, 24 of the catheter sidewall 16 are smooth. One exemplary PRIOR ART catheter is commercially known as the Cure Catheter™ 14 Fr., model number M405F1406, manufactured for and distributed by Cure Medical, LLC of Newport Beach, Calif.

Figure 20:
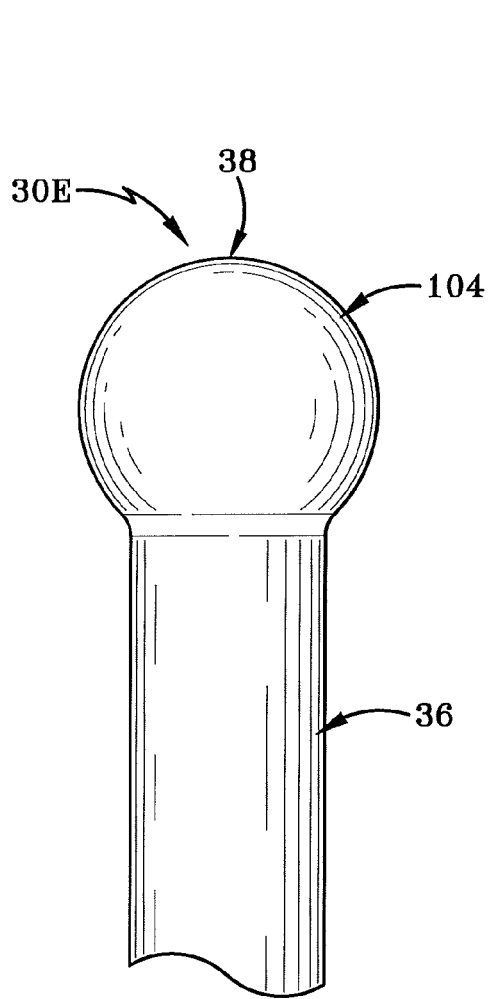
FIG. 20 is a side view of the first end of a fifth embodiment catheter.
Figure 21:
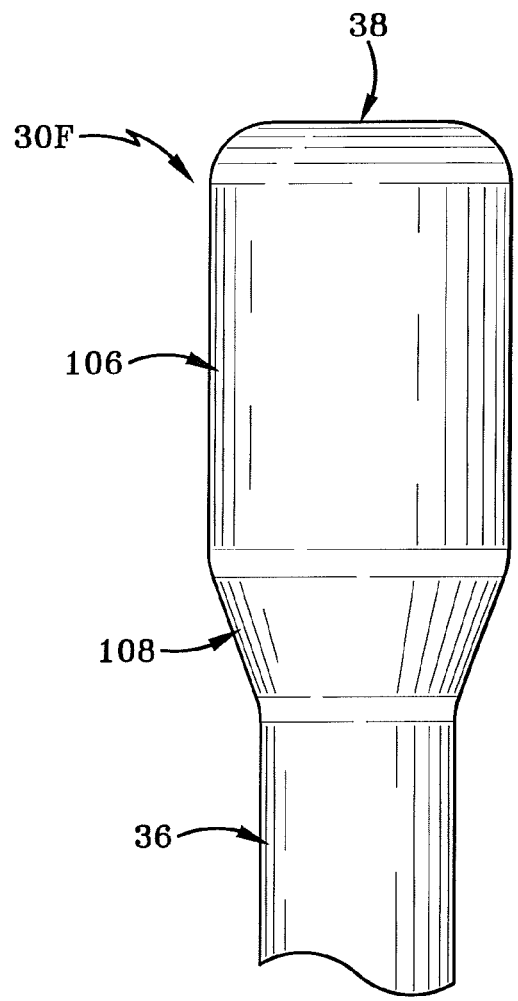
FIG. 21 is a side view of the first end of a sixth embodiment catheter.
Figure 24:
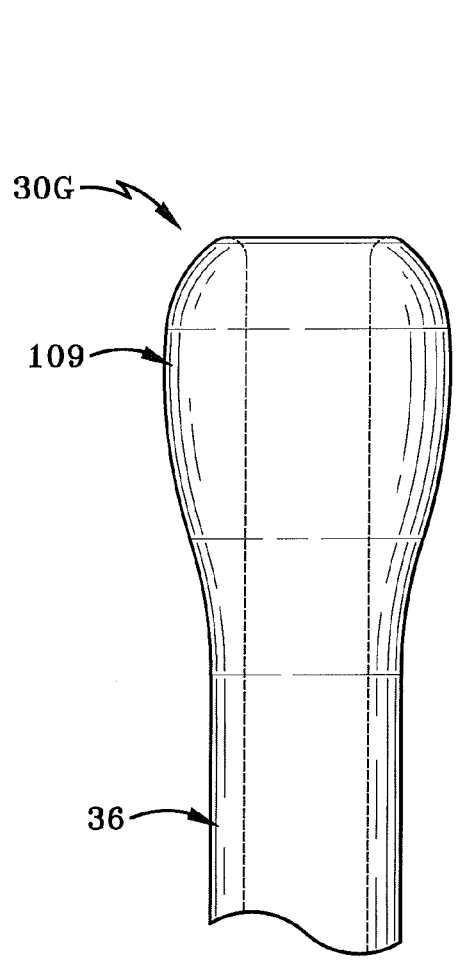
FIG. 24 is a side view of the first end of a seventh embodiment catheter.
Figure 25:
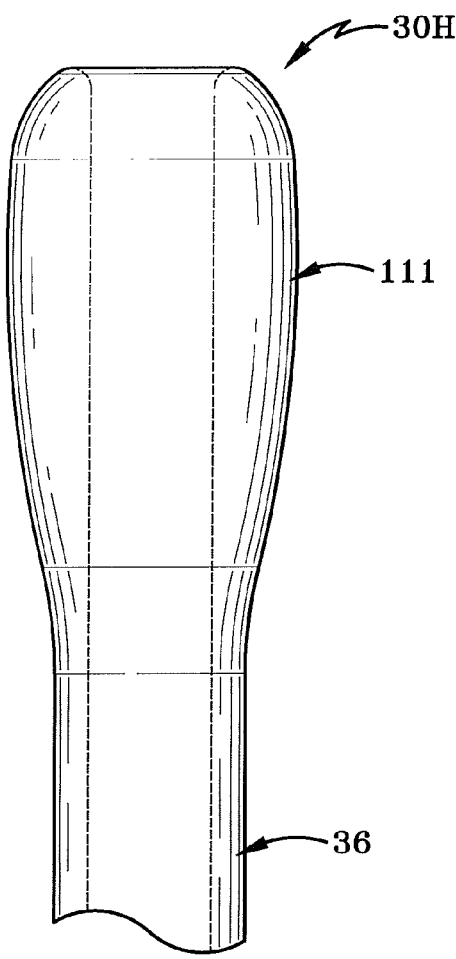
FIG. 25 is a side view of the first end of an eighth embodiment catheter.
Figure 26:
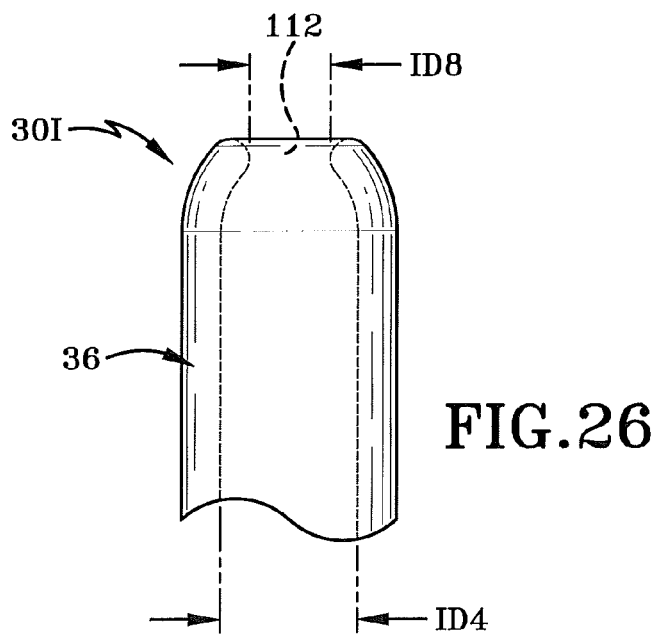
FIG. 26 is a side view of the first end of a ninth embodiment catheter.

The embodiments of the catheter of the present disclosure are identified using reference number 30A in FIGS. 4A-6B, 11A-11B, and 14A-14B; reference number 30B in FIGS. 7A-9B, 12, and 15; reference number 30C in FIGS. 10A-10C, 13, and 16; reference number 30D in FIGS. 17A-19C; reference numeral 30E in FIG. 20; reference numeral 30F in FIG. 21; reference number 30G in FIG. 24; reference number 30H in FIG. 25; and reference number 30I in FIG. 26.

As will be further described herein, first embodiment catheter 30A has a sidewall 36 that it of a substantially constant diameter from the first end of the catheter to the second end thereof. Second embodiment catheter 30B has a truncated tear-drop shaped first end; and third embodiment catheter 30C has a plurality of dimples on the outer surface of the catheter sidewall. Each embodiment may be configured so that a lumen defined in the catheter has any of five different interior surface configurations, each of which having a unique cross section.

With primary reference to FIGS. 4A-6B, catheter 30A has a catheter body or sidewall 36 (FIG. 3) comprising a top or first end 32, a bottom or second end 34 (FIG. 3), a first or right side 31, a second or left side 33, and an entrance opening 38 defined by the first end 32. Sidewall 36 has an outer surface 40 and an inner surface 42. A lumen 44 is defined by inner surface 42 and lumen 44 extends from first end 32 to second end 34 along a longitudinal axis X. First end 32 to second end 34 therebetween define a longitudinal direction. Right side 31 to left side 33 therebetween defines a radial direction. Catheter sidewall 36 is generally cannular or tubular and extends longitudinally, having a substantially constant outer diameter OD1 from first end 32 to second end 34 centered about longitudinal axis X as seen in device 30A of FIGS. 4A-5B.

Figure 4A:
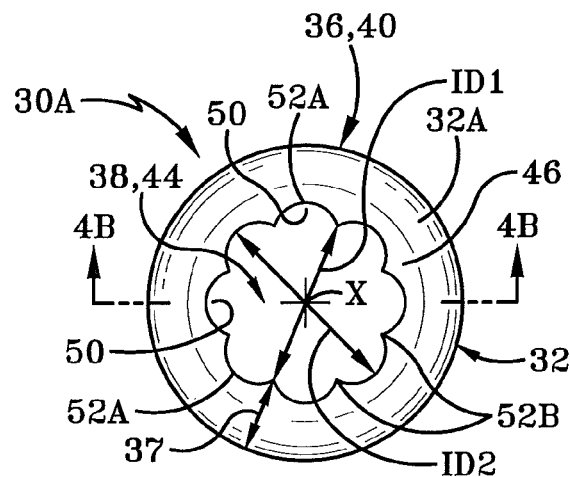
FIG. 4A is a top view of a first end of a first embodiment of the present disclosure depicting a catheter body which is of a substantially constant outer diameter along its length, and showing a first interior variation of a catheter lumen having an inner surface with connecting longitudinal channels.
Figure 4B:
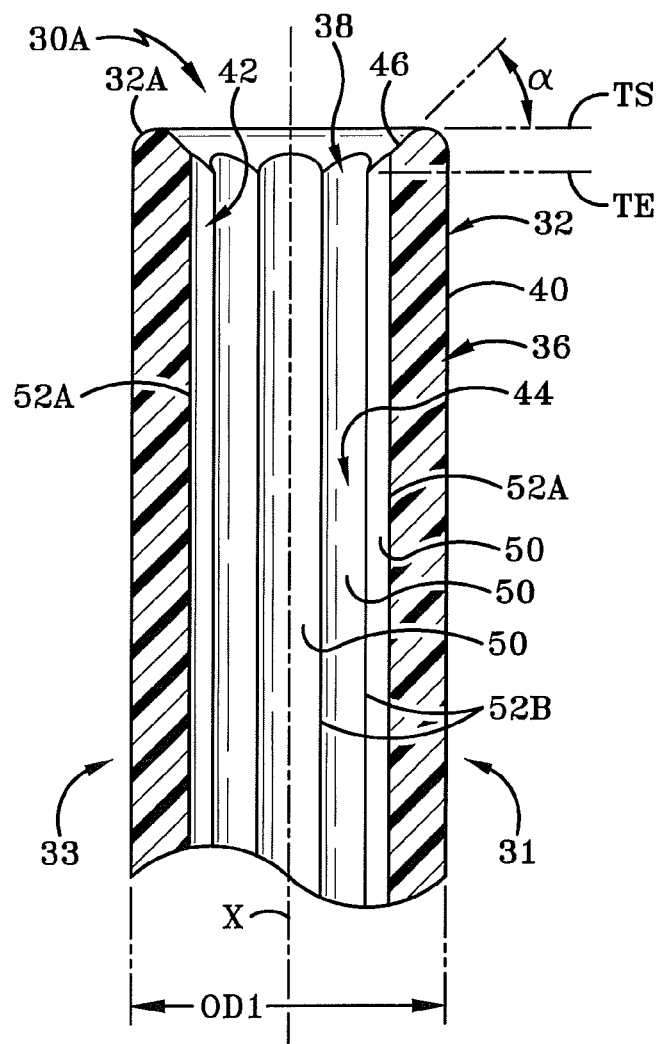
FIG. 4B is a cross section view taken along line 4B-4B in FIG. 4A.

In accordance with one aspect of the present disclosure, entrance opening 38 is defined by catheter sidewall 36 at the first end 32. Entrance opening 38 is a radial, inwardly tapering, through-opening which intersects the longitudinal axis X. Entrance opening 38 extends longitudinally from a tapered start plane TS to a tapered end plane TE. Tapered start plane TS is a radially extending plane at the top end of a tapered annular surface 46. Tapered end plane TE is a radially extending plane at the bottom end of surface 46. Entrance opening 38 is radially bound by surface 46. Preferably, planes TS, TE of entrance opening 38 intersect longitudinal axis X perpendicularly, however other angled relationships are contemplated. Entrance opening 38 has a diameter (ID1, ID2—FIG. 4A) that is substantially the same as the diameter (ID1, ID2—FIG. 4B) of lumen 4. Entrance opening 38 is in longitudinal alignment and in fluid communication with lumen 44. The term longitudinally aligned or longitudinal alignment herein refers to the entrance opening being positioned at the first end and permitting fluid to continue along the same path as lumen 44 without changing directions about longitudinal axis X. Surface 46 permits fluid to flow down the slope thereof and through entrance opening 38. Surface 46 is disposed at an angle α relative to longitudinal axis "X". Slope α begins at end wall 32A. End wall 32A is located at the first end 32 and comprises a rounded rim that is concentric with opening 38. Tapered start plane TS and end plane TE are each disposed at right angles to longitudinal axis X. As seen in FIGS. 4B, 5B slope α is shown at a 45 degree angle relative to tapered start plane TS, however slope α may be from about approximately 10 to about approximately 80 degrees relative thereto. Further, the taper of surface 46 generally requires sidewall thickness 37 to be approximately 25% greater in device 30A than a body thickness of a prior art catheter 10 having a substantially similar outer diameter.

Inner surface 42 may have five variations of cross sectional shapes or forms when viewed from the first end. It is to be understood that the five forms disclosed herein can be incorporated into any of the three embodiments of device 30A, 30B, and 30C. In a first form, inner surface 42 defines a plurality of channels 50 extending longitudinally and formed within the catheter sidewall 36. As seen in FIGS. 4B, 5B, channels 50 start in the surface 46 between the tapered start plane TS and tapered end plane TE. As shown in FIGS. 4A and 4B, channels 50 are defined by the longitudinally extending recesses 52A which are half-moon shaped when viewed from first end, connected along longitudinally extending edges 52B.

Figure 5A:
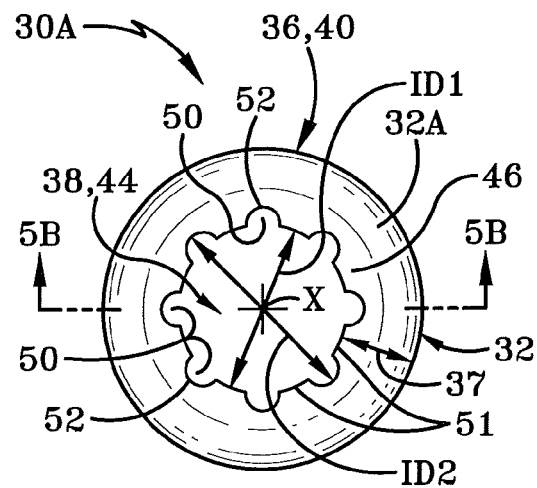
FIG. 5A is a top view of the first end of the first embodiment of the present disclosure depicting the constant outer diameter catheter body and showing a second variation of the lumen having spaced apart longitudinal channels along inner surface.
Figure 5B:
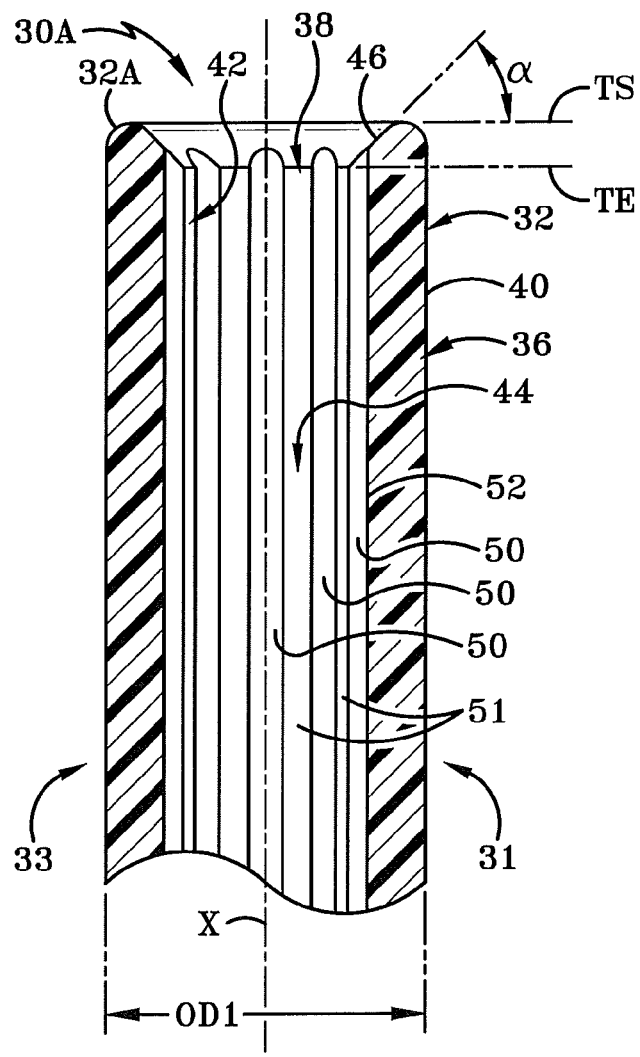
FIG. 5B is a cross section view taken along line 5B-5B in FIG. 5A.

In a second form, as shown in FIGS. 5A and 5B, the channels 50 can be defined by a plurality of longitudinally extending half-moon recesses 52 and arcuate separation sections 51. The half-moon recesses 52 or 52A are spaced annularly apart from one another in a manner so as to increase fluid flow through lumen 44 of catheter 30A relative to that of a conventional circular cross-sectional lumen known in the prior art. The separation sections 51 are generally equally spaced between the half-moon recesses 52.

Figure 6A:
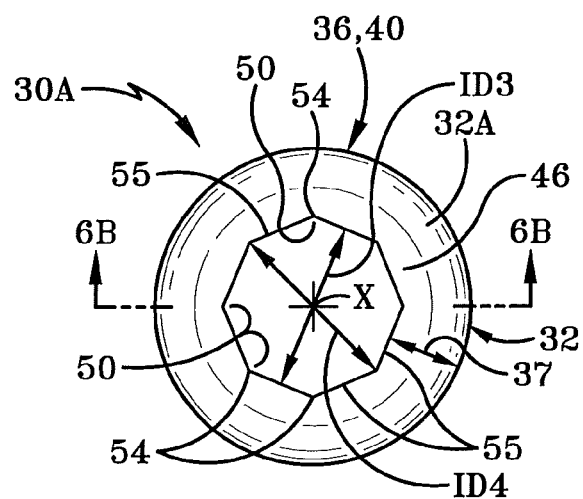
FIG. 6A is a top view of the first end of the first embodiment of the present disclosure depicting the constant outer diameter catheter body and showing a third variation of the lumen having a v-shaped channeled inner surface.
Figure 6B:
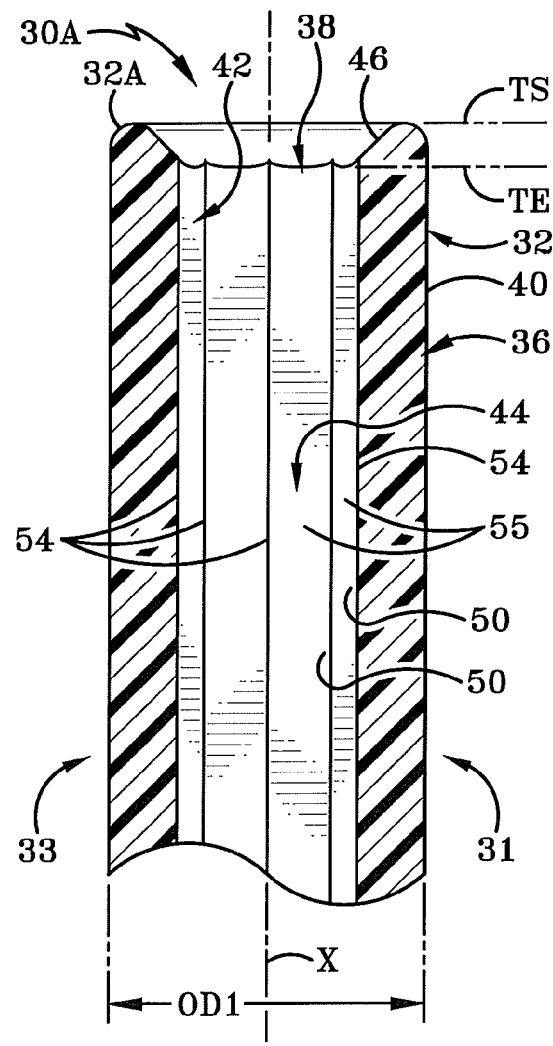
FIG. 6B is a cross section view taken along line 6B-6B in FIG. 6A.
Figure 7A:
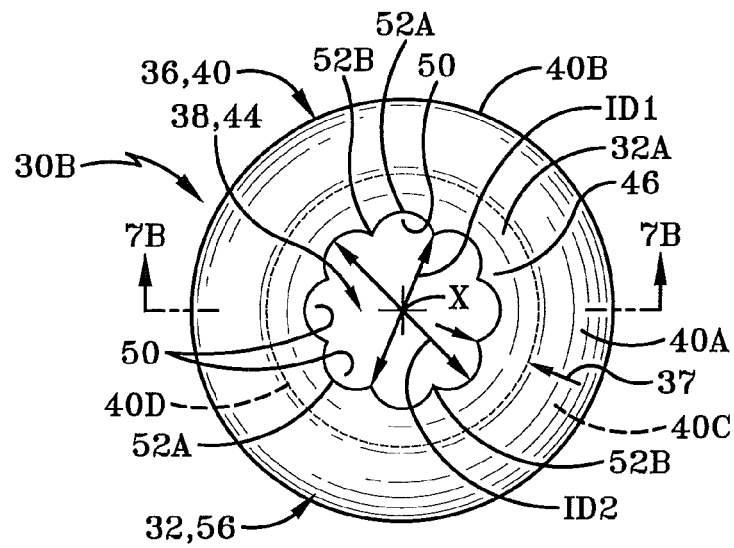
FIG. 7A is a top view of the first end of a second embodiment of the catheter depicting a truncated tear drop shaped head and the first interior variation of the inner surface having connecting annular channels.
Figure 7B:
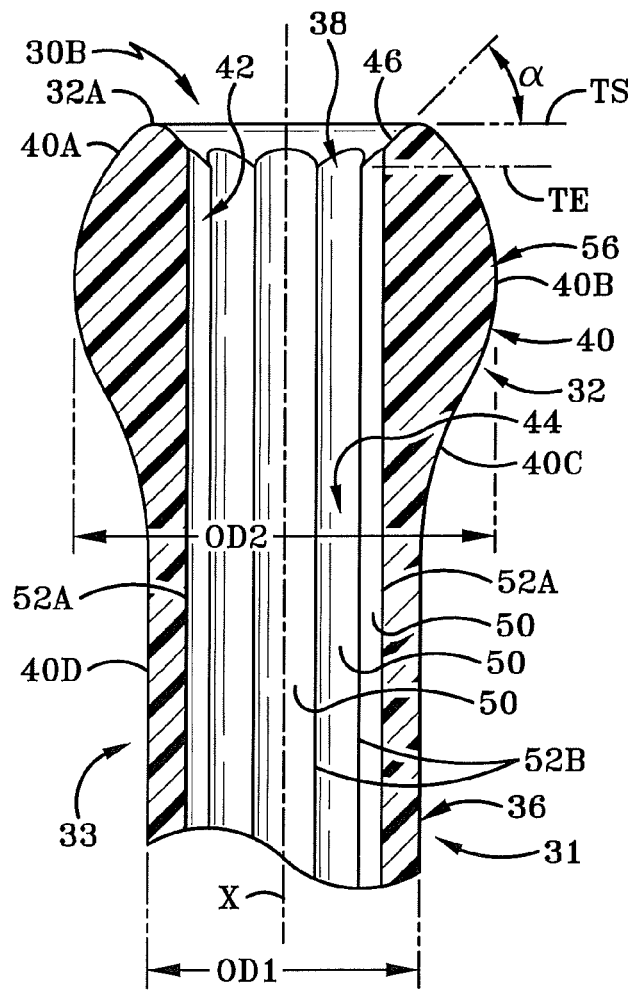
FIG. 7B is a cross section view taken along line 7B-7B in FIG. 7A.
Figure 8A:
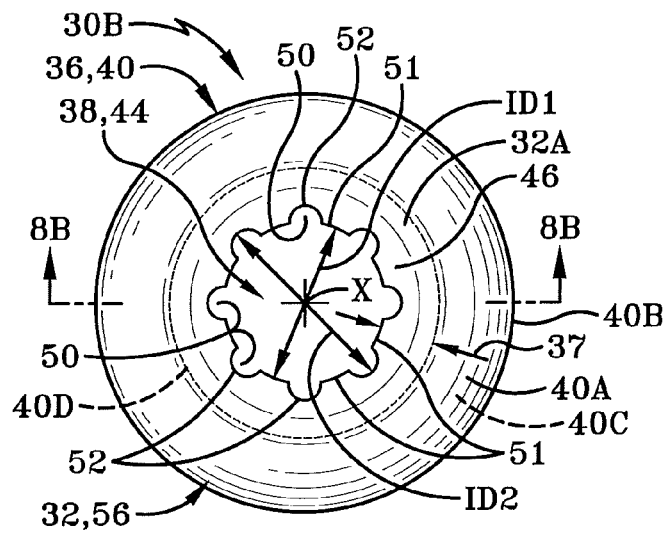
FIG. 8A is a top view of the second embodiment depicting the truncated tear drop shaped head with the second interior variation having the spaced apart annular channels along the inner surface.
Figure 8B:
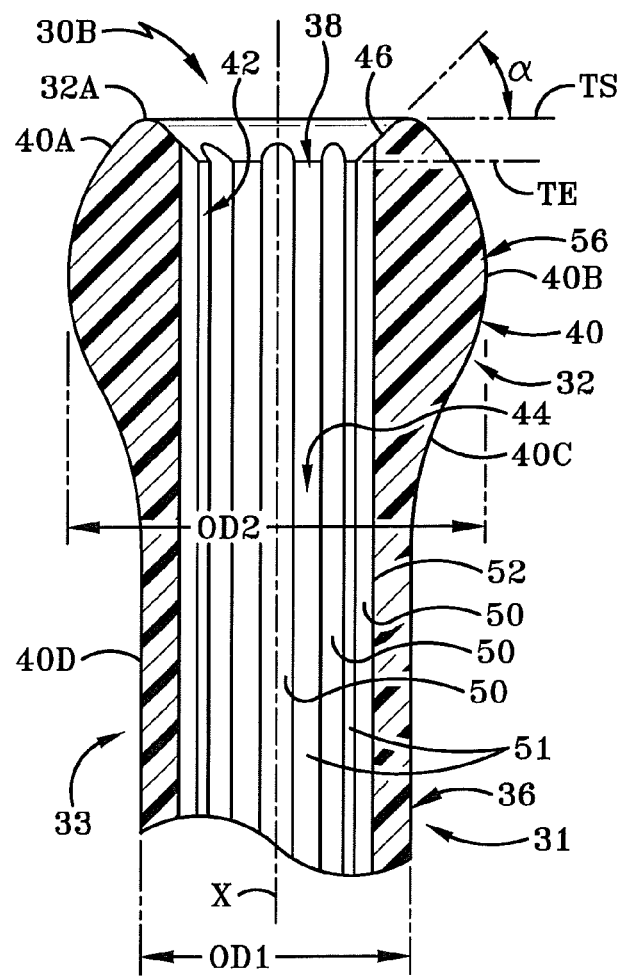
FIG. 8B is a cross section view taken along line 8B-8B in FIG. 8A.
Figure 9A:
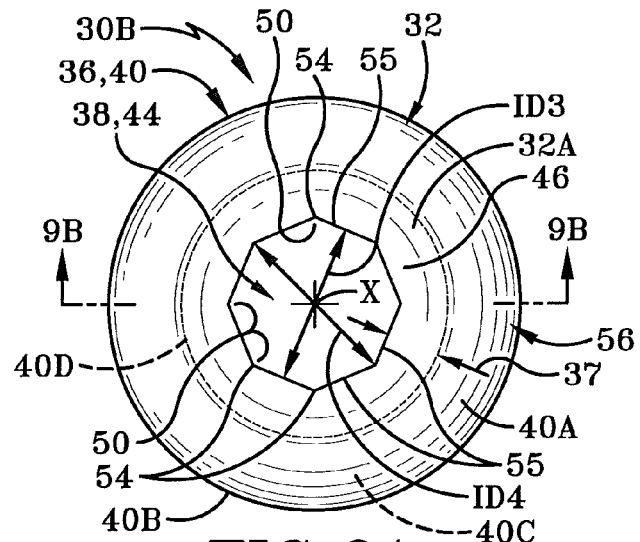
FIG. 9A is a top view of the second embodiment depicting the truncated tear-drop shaped head and the third variation of the lumen having the v-shaped channeled inner surface.
Figure 9B:
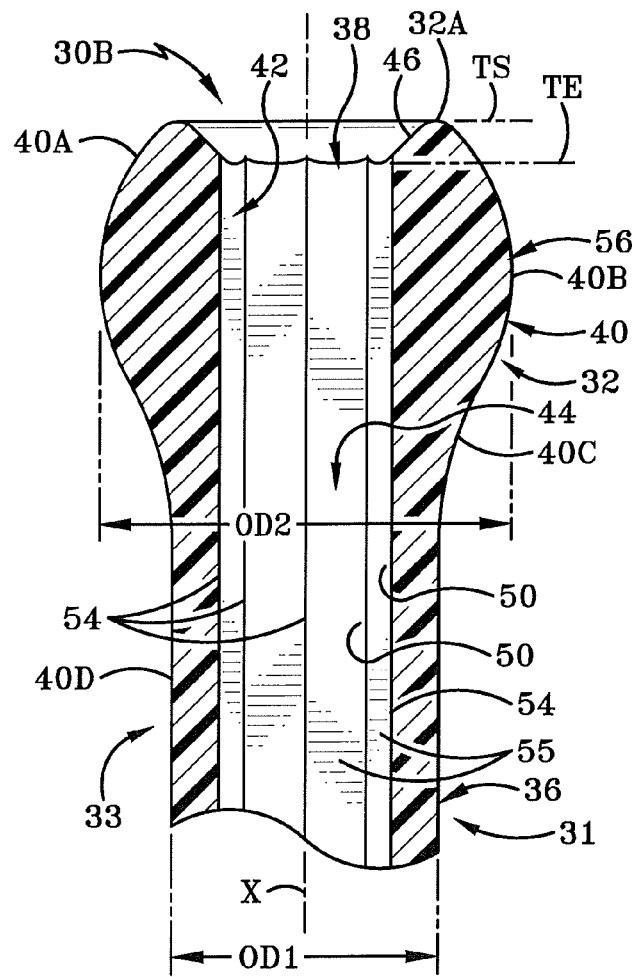
FIG. 9B is a cross section view taken along line 9B-9B in FIG. 9A.

In a third form, as shown in FIGS. 6A and 6B, channels 50 include at least one section that is straight or planar. In particular, each channel 50 preferably includes two straight sections that form a generally V-shaped channel defined by longitudinally extending edges 54 and connected flat panels 55 forming formed in the inner surface 42 in the catheter sidewall 36. The connected edges 54 and panels 55 provide a generally octagonal cross-section. While this embodiment provides a generally octagonal cross-section, yet other geometric shapes capable of being configured by connected edge 54 and panels 55 are contemplated. Further alternatively, channels 50 may be rifled to increase drainage flow rate. The term rifled in this context means channels 50 may extend concentrically in a helical manner from first end 32 to second end 34 along defined by inner surface 42.

Referring to FIGS. 4A-5B, 7A-8B sidewall 36 has an outer diameter shown as OD1 extending from right 31 to left 33 side of the surface, a first inner diameter shown as ID1, a second inner diameter shown as ID2, and a radial or sidewall thickness 37. Sidewall 36 may alternatively have a third inner diameter ID3 and a fourth inner diameter ID4 as seen in device 30A of FIGS. 6A-6B instead of the first and second inner diameters ID1, ID2. Further alternately, sidewall 36 may have a fifth inner diameter ID5 and a sixth inner diameter 106 as seen in device 30C of FIGS. 10A-10C instead of the first and second inner diameters ID1, ID2. Even further, sidewall 36 may have a single inner diameter, shown as ID7 in device FIG. 11A-16. Outer diameter OD1 extends from right side 31 to left side 33 of outer surface 40 as viewed from the cross section view in FIGS. 4B, 5B. As seen in the top view of FIG. 5A, first inner diameter ID1 extends radially across axis X between arcuate separation sections 51 and second inner diameter ID2 between half-moon recesses 52. As shown in the top view of FIG. 5B, third inner diameter ID3 extends radially across axis X between longitudinally extending panels 55 and fourth inner diameter ID4 extending radially between edges 54. As shown in the top view of FIG. 10A, fifth inner diameter ID5 extends radially across axis X from side to side 31, 33 of inner surface 42 and sixth inner diameter extends radially across axis X between dimples 62. As seen in FIGS. 4B, 5B, sidewall thickness 37 extends radially between outer surface 40 and inner surface 42. In any of the embodiment illustrated herein, it will be understood that the diameter of opening 38 is substantially of the same diameter of the lumen with which it is in fluid communication.

Ordinarily, catheters are characterized by a scale known as the "French Size", each French size having a corresponding outer diameter. For example, a catheter having a French Size 4 has an outer diameter of 0.053 inches or 1.35 mm. While a French Size 8 catheter has an outer diameter of 0.105 inches or 2.7 mm. Outer diameter OD1 of the present disclosure is configured to have the same outer diameter as a conventionally known French size.

With primary reference to FIGS. 7A-9B, a second embodiment of catheter 30B is shown having a bulbous or truncated teardrop-shaped head 56 formed in the first end 32 of the catheter sidewall 36. The truncated teardrop-shaped head 56 extends radially outwardly from longitudinal axis X to provide a second outer diameter OD2 that is larger than the outer diameter OD1 of sidewall 36. Outer surface 40 extends continuously along truncated teardrop-shaped head 56 having a first sloped surface 40A, an apex surface 40B, a second sloped surface 40C, and a sidewall surface 40D when viewed from the side. As seen in FIG. 7B, first sloped surface 40A extends a distance from rounded end wall 32A flared radially outward from axis X towards second end 34. Apex surface 40B is positioned below first sloped surface 40A when device 30B is oriented vertically. Apex surface 40B forms an apex from which the outer diameter OD2 of head 56 is determined. Second sloped surface 40C extends a distance from apex surface 40B flared radially inwards to axis X towards second end 34. Sidewall surface 40D continues from second sloped surface 40C to second end 34.

With continued reference to FIGS. 7A-9B, lumen 44 extends through the truncated teardrop-shaped head 56 in fluid communication with the entrance opening 38 as defined by its surface 46. Channels 50 have the same inner diameter extending from the entrance opening 38 through the truncated teardrop-shaped head 56 and continuing longitudinally through catheter sidewall 36.

With primary reference to FIGS. 10A-10C, the third embodiment catheter 30C has a plurality of convexly-shaped dimples 60 along outer surface 40, a plurality of concavely-shaped dimples 62 along inner surface 42, a plurality outer surface retention areas 43, a first outer diameter OD1, a second outer diameter OD3, first inner diameter ID5, second inner diameter ID6, in addition to other elements having similar reference numerals as the other embodiments. Catheter 30C may have a generally non-circular cross section or textured outer surface 40 and a generally non-circular cross section or textured inner surface 42. Convex dimples 60 are formed along the outer surface 40 in the catheter sidewall 36. The term convex with respect to dimples 60 refers to the dimples extending radially out of the catheter sidewall 36 and the dimple surface facing outward as viewed from above as seen in FIG. 10A. Convex dimples 60 have an outer annular edge 60A and an apex 60B. Annular edge 60A is a generally circular edge disposed where dimple 60 connects to outer surface 40 of sidewall 36. Apex 60B is the apex or radially outermost point of dimple 60 surface when viewed from a cross-sectional side view, as seen in FIG. 10C. Second outer diameter OD3 measures radially from right 31 to left 33 at mirroring apexes 60B. First outer diameter OD1 is the outer diameter of outer surface 40. Retention areas 43 are formed along and bound by the outer surface 40 and the spaces between annular edges 60A. Concave dimples 62 are formed along the inner surface 42 in catheter sidewall 36. The term concave with respect to dimples 62 refers to the dimples extending radially into the catheter sidewall 36.

Figure 11A:
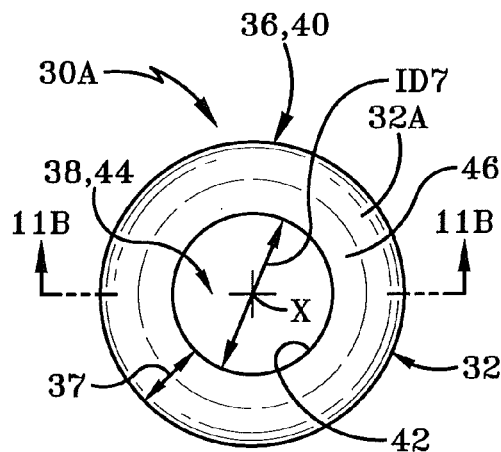
FIG. 11A is a top view of the first end of the first embodiment of the catheter depicting a fifth variation of the lumen and showing a smooth inner surface.
Figure 11B:
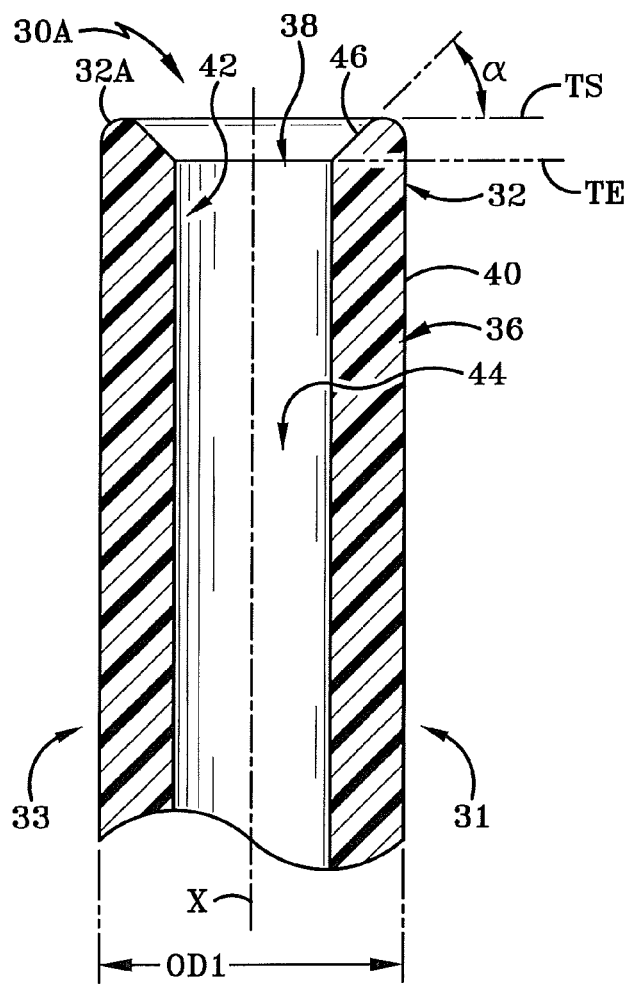
FIG. 11B is a cross section view taken along line 11B-11B in FIG. 11A.
Figure 12:
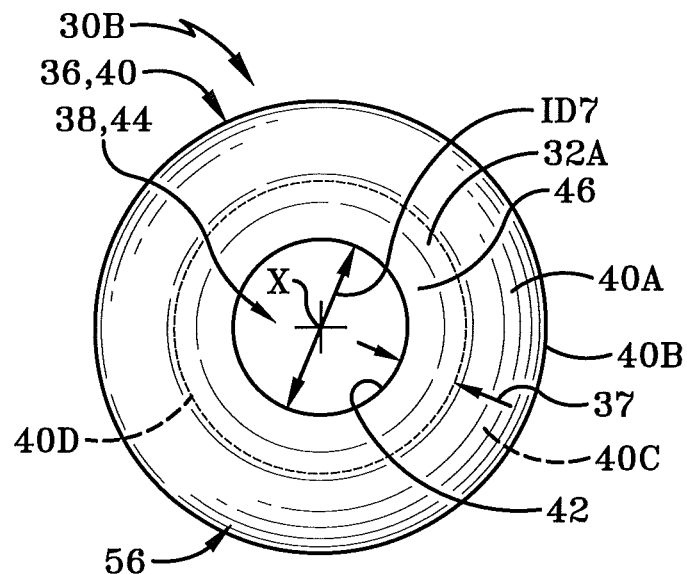
FIG. 12 is a top view of the first end of the second embodiment of the catheter and showing the fifth variation of the lumen having the smooth inner surface.
Figure 13:
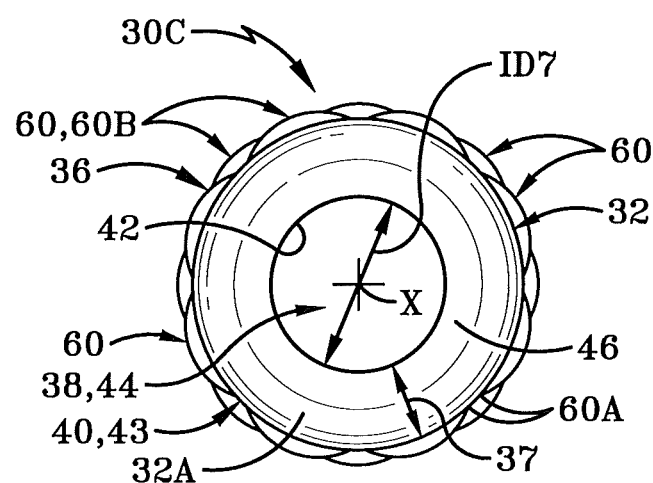
FIG. 13 is a top view of the first end of the third embodiment of the catheter depicting the fifth variation of the lumen having the smooth inner surface.
Figure 14A:
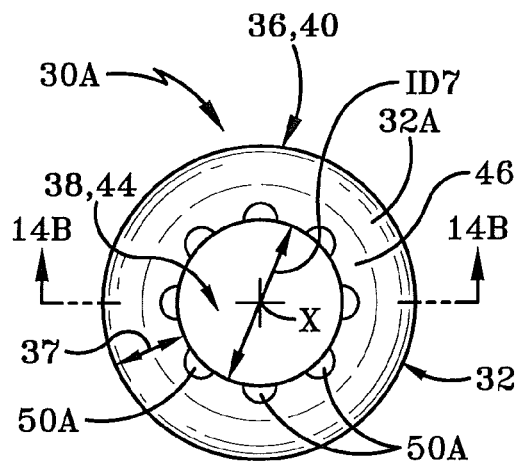
FIG. 14A is a top view of the first end of the first embodiment of the catheter and the fifth variation of the lumen and showing a plurality of spaced-apart friction or tension reducing cutouts positioned at the first end of the inner surface.
Figure 14B:
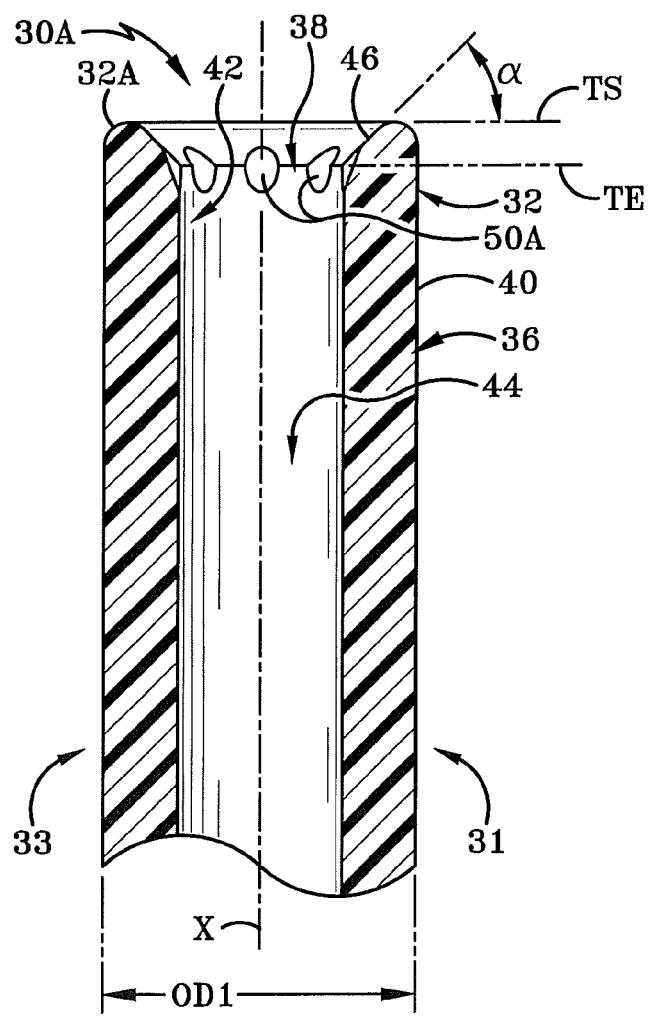
FIG. 14B is a cross section view along line 14B-14B in FIG. 14A.
Figure 15:
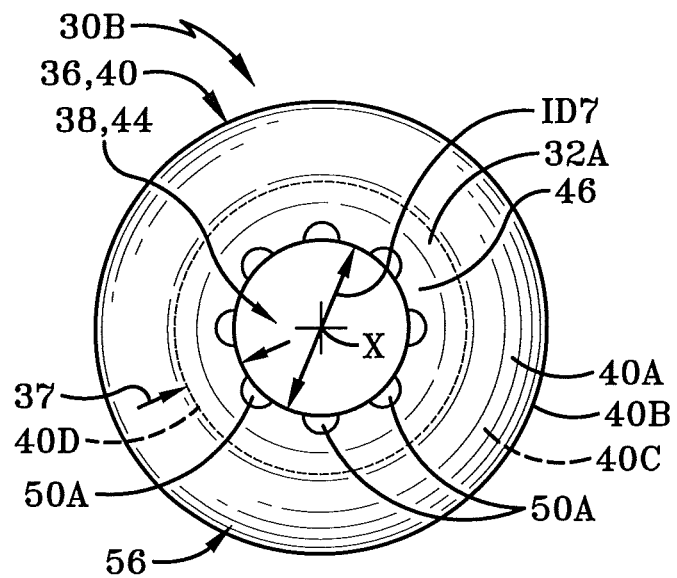
FIG. 15 is a top view of the first end of the second embodiment of the catheter having the fifth variation of the lumen and depicting the plurality of spaced apart friction or tension reducing cutouts positioned at the first end of the inner surface.
Figure 16:
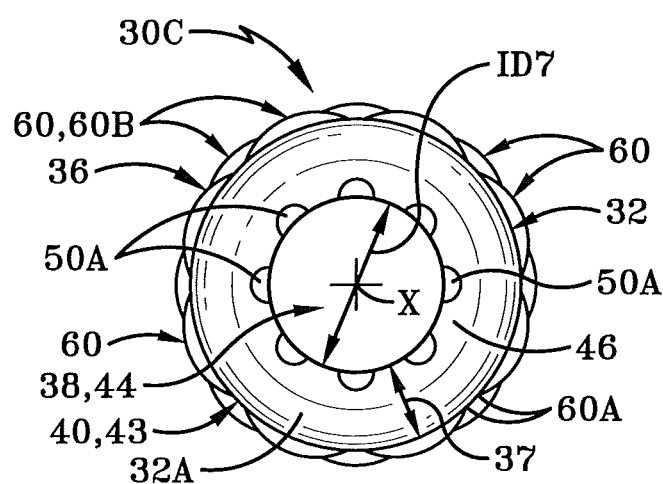
FIG. 16 is a top view of the first end of the third embodiment catheter having the fifth variation of the lumen and depicting the plurality of spaced apart friction or tension reducing cutouts positioned at the first end of the inner surface.

As seen in FIG. 11A-13, the catheter devices 30A, 30B, and 30C may have a substantially smooth inner surface 42 defining lumen 44 having only a single inner diameter ID7. The smooth inner surface 42 extends from first end 32 longitudinally to second end 34. As seen in FIGS. 11A, 12, and 13, inner surface 42 has a substantially circular cross section. Inner diameter ID7 is preferably generally equal to inner diameter ID1 in width. Alternatively as seen in FIGS. 14A-16, devices 30A, 30B, and 30C may have a substantially smooth inner surface 42 having an inner diameter ID7 in combination with a plurality of notches 50A. Notches 50A extend circumferentially around axis X and are formed in the first end 32 of sidewall 36. Notches 50A are preferably spaced circumferentially adjacent inner annular recess 46 aligned longitudinally along tapered end plane TE. Notches 50A function to reduce surface tension or fluid frictional forces as fluid flows through the entrance opening 38 into lumen 44 having a smooth surface. Preferably, notches 50A extend longitudinally only a short distance passed tapered end plane TE relative to the entire length of inner surface 42. Further preferably, notches 50A have a generally oval edge when viewed from the side (FIG. 14B) permitting notches to extend radially outward into the first end 32 of catheter sidewall 36.

As depicted in FIG. 17A-FIG. 19C, the embodiment of catheter 30D may include a generally flexible tubular body member 36 defining lumen 44 extending centrally along longitudinal axis X from the first end 32 to the second end 34 wherein the first end 32 is adapted to be inserted into the urethral canal 30 of the patient. Catheter 30D further includes an outer surface 69 spaced apart from inner surface 42. Inner surface 42 defines the lumen 44 which is adapted to drain fluid, namely urine, from the patient's bladder 71. Further, catheter 30D includes a plurality of distinct longitudinally extending convex surfaces 72 positioned circumferentially about longitudinal axis X that collectively define outer surface 69. In one embodiment of catheter 30D, convex surfaces 72 extend from adjacent first end 32 towards the second end 34 and in another embodiment of catheter 30D, the plurality of convex surfaces 72 begin at the first end 32 and extend towards the second end 34.

With continued reference to the plurality of convex surfaces 72 defining outer surface 69 of catheter 30D, a first convex surface 74 is positioned next to a second convex surface 76. First convex surface 74 extends arcuately from a first edge 78 to a second edge 80 and having an apex 82 between first edge 78 and second edge 80. First edge 78 and second edge 80 are spaced radially equidistant from longitudinal axis X. Apex 82 is spaced radially away from longitudinal axis X a distance greater than first edge 78 and second edge 80. Second convex surface 76 extends arcuately from first edge 84 to second edge 86 and has an apex 88 therebetween. First edge 84 and second edge 86 are radially equidistant to each other and preferably similarly dimensioned to first edge 78 and second edge 80. Additionally, apex 88 is spaced apart farther from longitudinal axis X than first edge 84 and second edge 86. In one embodiment, apex 88 is radially distanced from longitudinal axis X the same amount as apex 82.

Figure 17A:
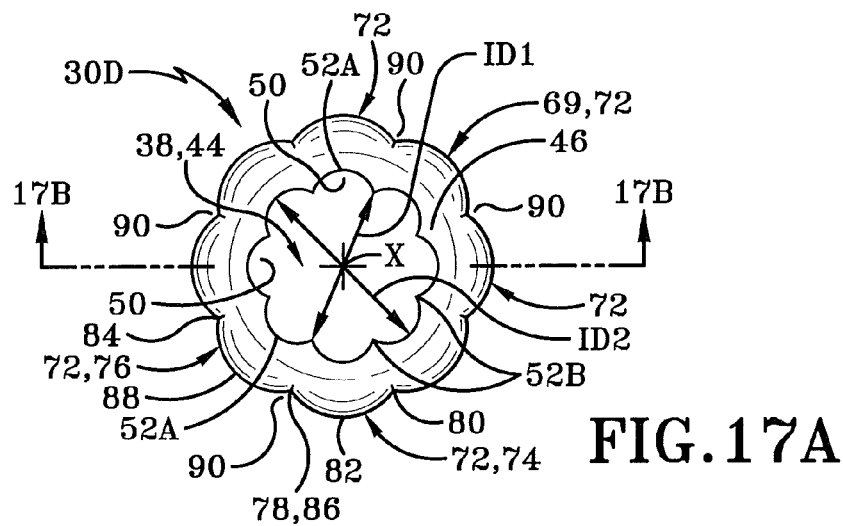
FIG. 17A is a top view of the first end of a fourth embodiment catheter having a plurality of distinct convex surfaces on the outer surface.
Figure 17B:
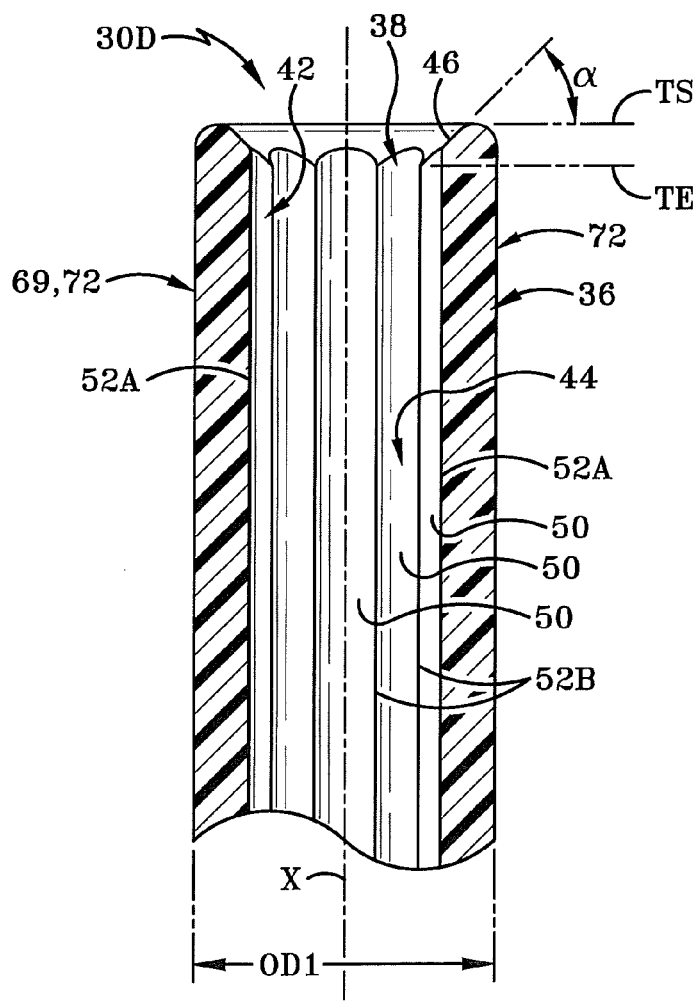
FIG. 17B is a cross section view taken along line 17B-17B in FIG. 17A.

Each one of the plurality of convex surfaces 72 arcuately extends at a radius of curvature. For ease of description, the radius of curvature is explained with reference to first convex surface 74, but applies to each one of the plurality of convex surfaces 72. The radius of curvature for convex surface 74 is determined by Equation (1):

$$R_{curv} = \frac{OD}{N} \qquad \text{Equation (1)}$$

wherein $R_{curv}$ equals the radius of curvature, OD equals the outer diameter of the catheter body measured across the outer surface (as shown in FIG. 17B, OD=OD1), and N equals the number of convex surfaces.

Recall, that the outer diameter of catheter depends on its French size. By way of non-limiting example, for a catheter having French Size 8 with an outer diameter {OD1 in FIG. 17a; OD for Equation (1)} of about 2.7 mm and eight convex surfaces 72 (as shown in FIG. 17a), the resulting radius of curvature ($R_{curv}$) for first convex surface 74 is ($R_{curv}$=2.7 mm/8 convex surfaces) about 0.33 mm. Additionally, by way of non-limiting example, for a French Size 4 catheter having an outer diameter {OD1 in FIG. 17a; OD for Equation (1)} of about 1.3 mm and eight convex surfaces 72 (as shown in FIG. 17a), the resulting radius of curvature ($R_{curv}$) for first convex surface 74 is ($R_{curv}$=1.33 mm/8 convex surfaces) about 0.16 mm.

Table 1 presents an example of some radii of curvature found by Equation (1). Are $R_{curv}$ values are presented in millimeters (mm).

TABLE 1

Exemplary $R_{curv}$ values

| French Size | OD (mm) | $R_{curv}$ for N = 4 | $R_{curv}$ for N = 6 | $R_{curv}$ for N = 8 | $R_{curv}$ for N = 10 | $R_{curv}$ for N = 12 |
|---|---|---|---|---|---|---|
| 4 | 1.33 | 0.333 | 0.222 | 0.166 | 0.133 | 0.111 |
| 6 | 2 | 0.500 | 0.333 | 0.250 | 0.200 | 0.167 |
| 8 | 2.667 | 0.667 | 0.445 | 0.333 | 0.267 | 0.222 |
| 10 | 3.333 | 0.833 | 0.556 | 0.417 | 0.333 | 0.278 |
| 12 | 4 | 1.000 | 0.667 | 0.500 | 0.400 | 0.333 |
| 14 | 4.667 | 1.167 | 0.778 | 0.583 | 0.467 | 0.389 |
| 16 | 5.33 | 1.333 | 0.888 | 0.666 | 0.533 | 0.444 |

Table 1 indicates that a radius of curvature for one of the plurality of distinct convex surfaces 72 may be generally in a range from about 0.1 mm to about 1.33 mm.

As depicted in FIG. 17A, all convex surfaces 72 have the same radius of curvature, however other particular embodiments is possible and may even be desired to have differing radii of curvature associated with different ones of the plurality of convex surfaces 72.

First edge 78 of first convex surface 74 connects with second edge 86 of second convex surface 76 to define a longitudinally extending channel 90 therebetween. In the embodiment shown in FIG. 17A and FIG. 17B, channel 90 begins at the first end 32 of catheter 30D and extends towards the second end 34. However in some other embodiments, channel 90 may begin closely adjacent the first end 32 and extend towards the second end 34. Channel 90 is configured to retain a gel based lubricant therein as catheter 30D is advanced through the urethral canal towards the patient's bladder. The lubricant may be applied manually by the patient or in some other embodiments a gel-based lubricant may be pre-packaged inside the catheter packaging such that when the catheter is advanced through an end of the packaging, as it moves through the gel-based lubricant where the gel-based lubricant is retained in channel 90.

Additionally, as depicted in FIG. 17A, channel(s) 90 exists and are defined at each location where one of the plurality of convex surfaces 72 contacts and meets another convex surface circumferentially next to it relative to longitudinal axis X. Thus, while eight channels 90 are depicted in FIG. 17A, it is to be clearly understood that alternative configurations are entirely possible. For example, the plurality of convex surfaces 72 may define four channels 90, or five channels 90, or six channels 90, or seven channels 90, or nine channels 90, or ten channels 90, or eleven channels 90, or twelve channels 90, and so on. Furthermore, catheter 30D depicts eight convex surfaces 72 and eight inner concave channels 50. It is to be understood that the number of concave inner channels 50 does not need to equal the number of convex outer surfaces 72. It is entirely possible to have four inner concave channels 50 and twelve outer convex surfaces 72 on catheter 30D. Similarly, catheter 30D may have four outer convex surfaces 72 and twelve inner concave channels 50. Or, any combination therebetween. The optimized configuration of catheter 30D is dependent on the French size and the desired flow rate for urine leaving the bladder.

As depicted in FIG. 18A and FIG. 18B, catheter 30D may include an enlarged bulbous head 92 having an outer diameter OD2 greater than an outer diameter OD1 of catheter body 36. The plurality of convex outer surfaces 72 begin at the first end of catheter 30D and extend over the enlarged head 92. Additionally, the channels 90 are formed along enlarged head 92.

With continued reference to FIG. 18A, a first apex 94 is disposed circumferentially from a second apex 96 on head 92. First and second apexes 94, 96 are farther away from longitudinal axis X than apex 82 and apex 88 on catheter body 36.

As depicted in FIG. 19A and FIG. 19B, an embodiment of catheter 30D includes a bulbous head 100. Bulbous head 100 has an outer diameter OD2 greater than outer diameter OD1 of outer surface 69 on catheter body 36. In the embodiment shown in FIG. 19A, the plurality of convex outer surfaces 72 and channels 90 defined therebetween are disposed entirely to one side of bulbous head 100. As depicted in FIG. 19B, convex surfaces 72 being below head 100 such that head 100 includes a substantially smooth and continuous outer surface 102.

As depicted in FIG. 18C and FIG. 19C, outer surface 69 of catheter body 36 including the plurality of convex surfaces 72 has a flower petal-like configuration when viewed in cross-section. Additionally, tubular body 36 in some embodiments may be completely free of openings extending through said body 36 such that the only opening in catheter 30D is entrance opening 38 intersecting longitudinal axis X.

As depicted in FIG. 20, an embodiment of catheter 30E depicts a spherical head 104 formed adjacent the first end of the tubular body member 36 wherein the spherical enlarged head 104 has a diameter greater than that of tubular body 36. The enlarged head 104 on catheter 30E is adapted to guide intermittent urinary catheter 30E through the urethral canal of a patient.

As depicted in FIG. 21, an embodiment of catheter 30F depicts an enlarged head 106 that is generally cylindrical having a uniform diameter along the longitudinal length of head 106. Enlarged cylindrical head 106 may be connected to catheter body 36 via a tapered step down section 108. The cylindrical tip 106 is formed adjacent the first end of catheter 30E and has an outer diameter greater than that of tubular body member 36. Cylindrical tip 106 is adapted to guide the intermittent urinary catheter 30F through the urethral canal of a patient.

As depicted in FIG. 24, an embodiment of catheter 30G includes an enlarged head 109 having a maximum diameter width offset from an imaginary horizontal midline of head 109. Stated otherwise, the bulbous head 109 on catheter 30G has its widest point closely adjacent the first end. The head 109 then tapers inwardly towards the catheter body 36. Head 109 may be configured to have a plurality of convex sections or portion extending there-along, similar to the other embodiment catheters disclosed above. Further, the interior lumen may be defined by any of the described configurations presented above.

As depicted in FIG. 25, an embodiment of catheter 30H depicts an enlarged head having a maximum diameter width offset from an imaginary horizontal midline of head 111. Stated otherwise, the bulbous head 111 on catheter 30H has its widest point closely adjacent the first end. Head 111 is more elongated than head 109. Head 111 tapers at a lower tapering angle relative to body 36 than shown on catheter 30G. Head 111 may be configured to have a plurality of convex sections or portion extending there-along, similar to the other embodiment catheters disclosed above. Further, the interior lumen may be defined by any of the described configurations presented above.

As depicted in FIG. 26, an embodiment of catheter 30I depicts an end of the catheter body 36 tapering inwardly (i.e., towards the longitudinally extending center axis). The inwardly tapering end of catheter 30I defines an entrance opening 112 of the intermittent catheter 30I having a diameter ID8 perpendicularly intersecting the longitudinal axis that is less than the inner diameter ID4 of the lumen. The inwardly curving end of catheter 30I provides strength to the first end. Further, the opening 112 having diameter ID8 less than inner diameter ID4 of lumen may have a venturi-like effect (e.g., increase velocity while decreasing pressure) on the urine draining from the bladder as it enters catheter 30I and moves through opening 112. Opening 112 is aligned along the same longitudinal axis as the lumen of catheter 30I. Opening 112 is distinct from a conventional "eyelet" on a catheter inasmuch as it does not extend radially through the catheter body, rather is defined by an end and extends longitudinally.

Figure 27:
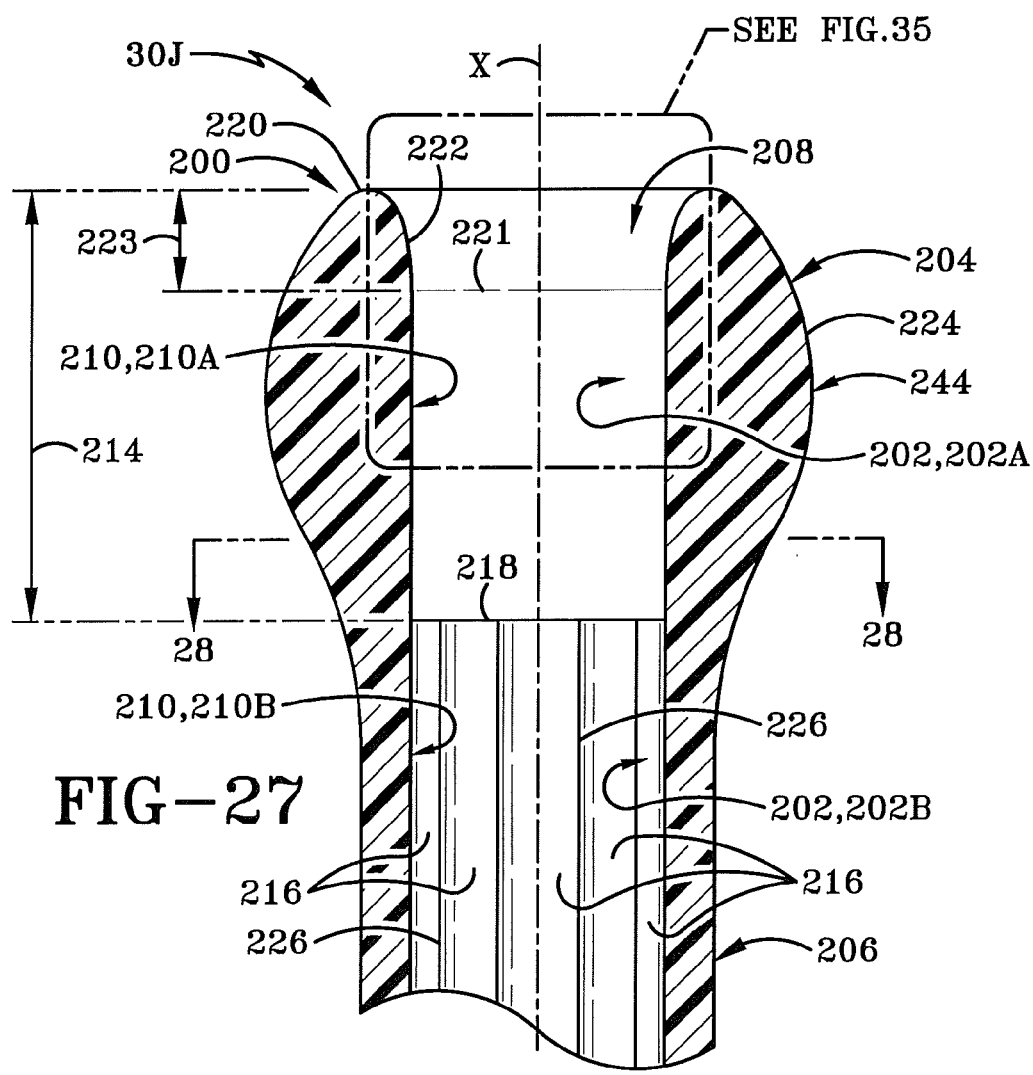
FIG. 27 is an enlarged cross-sectional view of the first end of a tenth embodiment catheter.

FIG. 27 depicts another embodiment of a catheter 30J in accordance with one aspect of the present disclosure. Catheter 30J includes a first end 200 spaced apart from a second end (not shown) defining a lumen 202 extending longitudinally therebetween along the longitudinal axis X of the catheter 30J. The catheter 30J further includes enlarged head 204 having a diameter greater than that of the tubular body 206.

Figure 28:
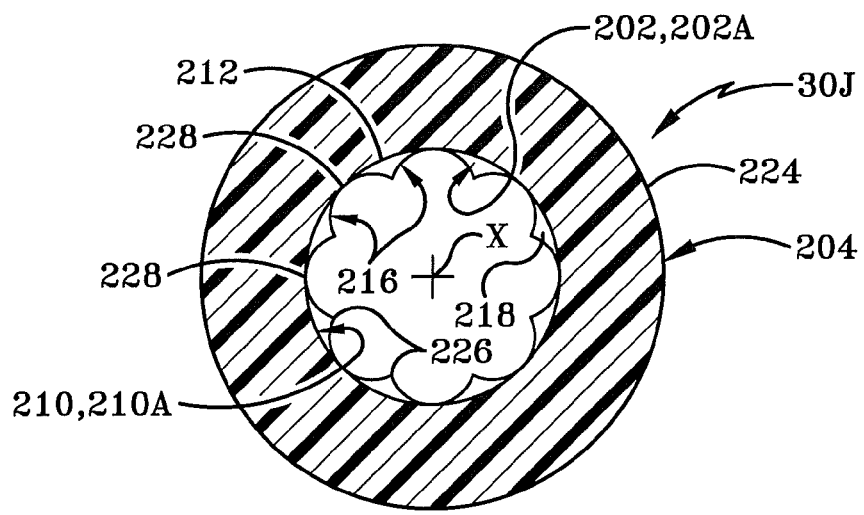
FIG. 28 is a cross-section view of the tenth embodiment catheter taken along line 28-28 in FIG. 27.

Catheter 30J further includes an opening 208 in fluid communication with the lumen 202 and the opening 208 is generally orthogonal to the longitudinal axis X and defined adjacent or at the first end 200 of catheter 30J. As will be described in greater detail below with reference to FIG. 35, the inner surface of the catheter 30J defining the opening 208 has a curved profile to allow fluid to flow or transition through the opening into the lumen 202. Lumen 202 includes a first portion 202A and a second portion 202B. First portion 202A is located proximal to the first end 200 of catheter 30J and the second section 202B of lumen 202 is located farther away from first end 200. The lumen 202 is defined by an inner surface 210 the tubular body member of catheter 30J. The inner surface 210 defining lumen 202 includes a first section 210A and a second section 210B. The inner surface first section 210A defines the lumen first section 202A and is smooth and does not contain any channels such that section 210A has a circular cross-section represented by the profile line 212 (FIG. 28). The inner surface first section 210A has a longitudinal length represented by 214 which also corresponds to the length of the enlarged head 204.

The inner surface second section 210B which defines the second section 202B of lumen 202 includes a plurality of arcuately concave surfaces defining channels 216 extending longitudinally and collectively defining a portion of the inner surface of catheter 30J.

The channels 216 formed in second section 210B of inner surface 210 meet the first section 210A at a ledge 218. The ledge 218 extends inwardly from the inner surface 210B generally orthogonal relative to the longitudinal axis of the catheter 30J. The smooth cylindrical bore of the first section 210A of the inner surface 210 is entirely offset towards the first end 200 from ledge 218. The ledge 218 may be considered a transition area or transition zone where the smooth bore of the first section 210A of inner surface 210 transitions to the channelized portion of the second section 210B of the inner surface 210.

In accordance with one aspect of the present disclosure, the first section 210A having a smooth surface that is circular in cross-section provides a functional relationship for catheter 30J when draining urine from a patient's bladder. Namely, as the first end 200 of the catheter 30J is advanced through the urethral canal and is inserted into the bladder to provide fluid communication to the lumen such that the catheter 30J drains the bladder. However, in some instances, a patient may inadvertently advance the catheter too far such that the first end 200 of catheter 30J contacts a bladder sidewall. In such a scenario, a portion of the bladder sidewall may be inadvertently sucked into the lumen 202 through opening 208. The smooth surface that is circular in cross section of the first section 210A of inner sidewall 210 (collectively with a rounded end wall 220 and connected with a rounded transition wall 222) ensure that the bladder sidewall of the patient is not cut, damaged, or otherwise injured. The rounded transition wall 222 extends in a tapering manner from the rounded end wall 220 towards the longitudinal axis X in an arcuately convex configuration. The transitional wall 222 terminates at an end plane 221 that is orthogonal to the longitudinal axis X. The end plane 221 is positioned offset towards the first end relative to an apex 244 of the enlarged head 204. The longitudinal length of the transition zone 222 is measured from the rounded end wall 220 to the end plane 221 and the distance is represented by distance 223. Stated otherwise, the configuration of the rounded end wall 220, the rounded transition wall 222, and the smooth first section 210A of inner surface 210 provide an atraumatic entrance opening to catheter 30J while still providing the improved drainage features of the arcuate concave surfaces defining channels 216 in the lumen second section 202B.

As depicted in FIG. 28, the tubular body 206 of catheter 30J has a sidewall thickness bound between the outer surface 224 and the inner surface 210. Catheter 30J may be formed in a similar manner to the other catheters disclosed herein with the plurality of distinct longitudinally extending convex surfaces 72 positioned circumferentially about longitudinal axis X that collectively define outer surface of the tubular body 206. As indicated previously, the inner surface 210 in first section 210A is close to first end 200 defining circular profile 212 and the channels formed in the second section 210B define a ledge 218 therebetween. The ledge 218 extends inwardly from inner surface 210 near an orthogonal plane where the enlarged head 204 transitions into the normal diameter of the tubular body 206. FIG. 28 further depicts that there are a plurality of channels 216 formed in the second section 210B of inner surface 210. While eight channels are depicted in FIG. 28, it is to be understood that alternative numbers of channels be provided. Moreover, in one particular embodiment, the number of channels 216 formed in catheter 30J is an odd number of channels. More specifically, a catheter 30J having a French size in a range from French 4 to French 8 may have five channels 216 formed in second section 210B of inner surface 210. Another exemplary embodiment of the catheter 30J having a French size relative to the tubular body 206 in a range from French size 10 to French size 16 may have seven channels 216 formed in the second section 210B of inner surface 210.

With continued reference to FIG. 28, catheter 30J may have a distinguishing feature of the outermost portion of each channel 216 being at the same radial distance relative to the circular profile 212 of the inner surface 210 of the first section 210A. Stated otherwise, the convex channels 216 extend inwardly towards the longitudinal axis X such that their end points 226 are radially closer to the longitudinal axis X and their outermost point 228. In this configuration, since the outermost region 228 of each channel 216 is radially coplanar with the smooth inner surface of the first section 210A, it is seen that no portion of the channel 216 extends inwardly into the tubular body 206 of catheter 30J. Stated otherwise, the ledge 218 extends inwardly into the lumen 202 and not into the tubular body 206.

Figure 29:
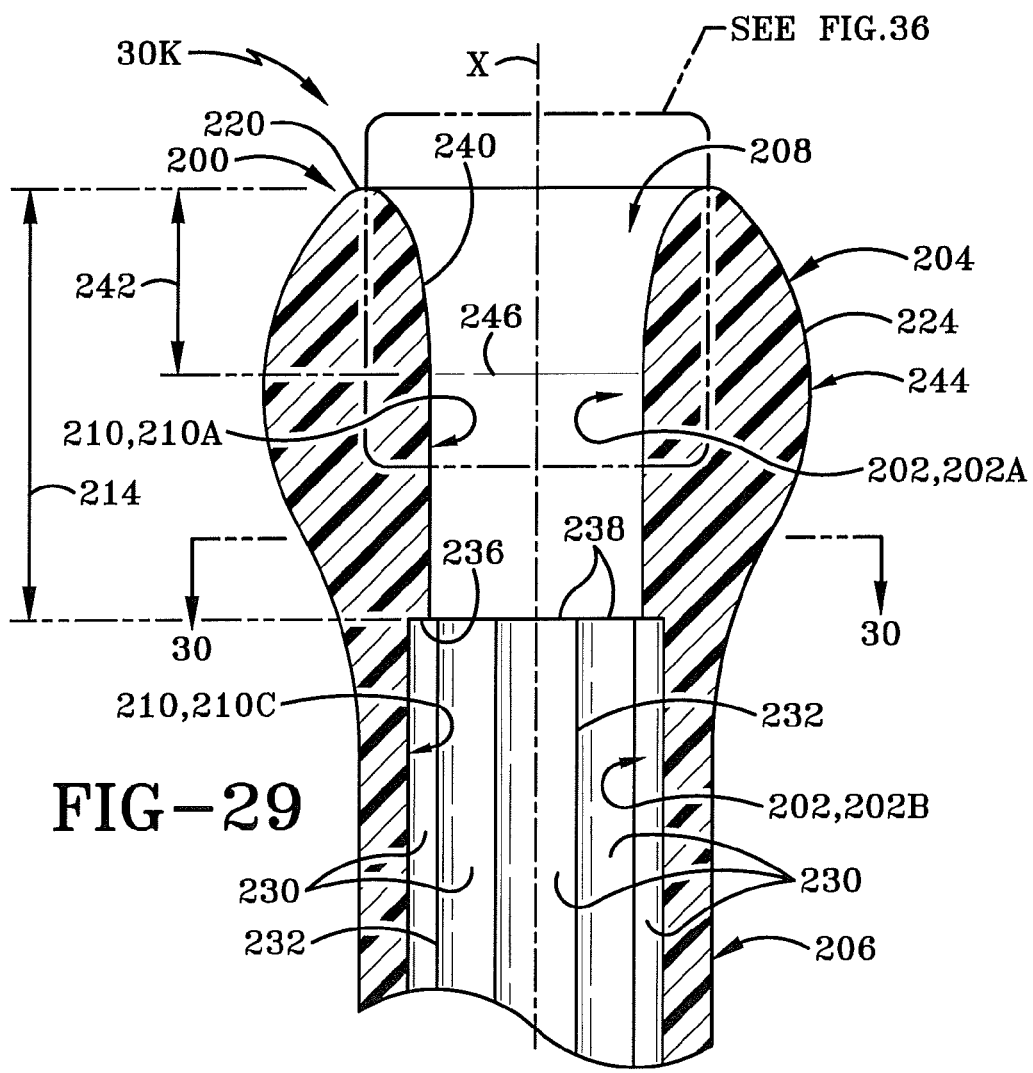
FIG. 29 is an enlarged cross-section view of the first end of an eleventh embodiment catheter.

As depicted in FIG. 29, another embodiment of a catheter in accordance with the present disclosure is shown generally as 30K. Catheter 30K includes some features that are similar to those identified in FIG. 27 and the similar features have similar reference numerals and are not repeated herein for brevity. Catheter 30K defines lumen 202 including a first lumen section 202A and a second lumen section 202B. First lumen section 202A is defined by a first section 210A of an inner surface 210 of catheter 30A. The second lumen section 202B of lumen 202 is defined by a second section 210C of the inner surface 210. Second section 210C defines a plurality of channels 230 extending longitudinally and concentric around longitudinal axis X. Channels 230 include arcuately concave inwardly facing surfaces that extend into the tubular body 206 such that an innermost end point 232 (FIG. 30) is radially aligned with the circular profile 212 of first section 210A. Since the channels 230 extend into the body 206 entirely offset from enlarged head 204, a radial outermost point 234 (FIG. 30) extends into the tubular body 206 defining a transition ledge 236 to the top 238 of the channels 230. Further, catheter 30K may be formed in a similar manner to the other catheters disclosed herein with the plurality of distinct longitudinally extending convex surfaces 72 positioned circumferentially about longitudinal axis X that collectively define outer surface of the tubular body 206.

An arcuately convex transitional wall 240 on catheter 30K terminates at an orthogonal end plane 246 relative to longitudinal axis X. The apex of enlarged head 204 is approximately coplanar with end plane 246 relative to the longitudinal axis X. The first section 210A of inner surface 210 positioned intermediate end plane 246 and transitional ledge 236. Inner surface 210 in the first section 210A is smooth having the rounded profile 212 (i.e., a circular cross-section) intermediate end plane 246 and channels 230.

Figure 30:
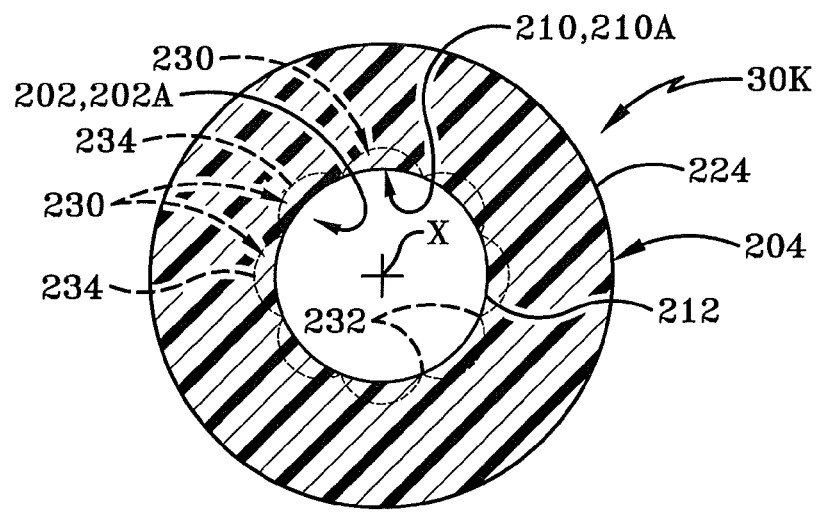
FIG. 30 is a cross-section view taken along line 30-30 in FIG. 29 of the eleventh embodiment catheter.

FIG. 30 depicts the view from the first end looking towards the second end of the lumen 202 wherein the circular profile 212 of the smooth surface of the first section 210A of inner surface 210 block the view of the arcuately concave channels 230 such that the channel walls 230 are hidden from view, but fluid will transition over the ledge 236 downwardly through the lumen to exit the second end of the catheter 30K.

FIG. 31 depicts a catheter 30L having some similar features to those catheters described above wherein similar reference numerals apply to similar elements and are not repeated herein for brevity. Catheter 30L includes first section 210A of inner surface 210 defining a smooth cylindrical inner sidewall having a circular cross-section and defining a first portion 202A of lumen 202. Second section 210B of inner surface 210 includes a plurality of channels 216 extending longitudinally from an end plane 248 orthogonal to longitudinal axis X. A beveled or sloped edge 250 extends inwardly from plane 248 to effectuate a transition from the smooth inner surface of first section 210A to the channels of second section 210B of inner surface 210. Similar to catheter 30J, the channels have a radial outermost portion that does not extend into the cylindrical sidewall of the tubular body 206. Rather, radial innermost edges 226 extend inwardly or closest to the longitudinal axis X. Further, catheter 30L may be formed in a similar manner to the other catheters disclosed herein with the plurality of distinct longitudinally extending convex surfaces 72 positioned circumferentially about longitudinal axis X that collectively define outer surface of the tubular body 206.

FIG. 32 depicts another exemplary catheter in accordance with the present disclosure generally at 30M. Catheter 30M includes the rounded convex transitional wall 240 similar to that of catheter 30K depicted in FIG. 29. The smooth cylindrical inner surface 210 of the first section 210A that transitions into a second section 210C that forms channels that extend inwardly into the sidewall of tubular body 206. However, unlike catheter 30K, the catheter of 30M in FIG. 32 includes an angled wall 252 extending longitudinally outward relative to axis X and into the tubular body 206. The beveled wall 252 extends towards the second end of catheter 30M from a plane 254. Similar to FIG. 30, since the channels 230 extend inwardly into the body of the tubular body 206, the radial innermost edge 232 is radially equal with the circular profile 212 of the inner surface 210A relative to the longitudinal axis X. Further, catheter 30M may be formed in a similar manner to the other catheters disclosed herein with the plurality of distinct longitudinally extending convex surfaces 72 positioned circumferentially about longitudinal axis X that collectively define outer surface of the tubular body 206.

FIG. 33 depicts another exemplary embodiment of a catheter in accordance with the present disclosure. Catheter 30N includes a first end 200 opposite a second end (not shown) and the longitudinal axis X extending therebetween.

A first section 210A of inner surface 210 defines a first portion 202A of lumen 202 and a second section 210B of inner surface 210 defines a second portion 202B of lumen 202.

Catheter 30N further comprises an outer surface 256 forming a generally cylindrical sidewall from the first end 200 to the second end of catheter 30N. Further, catheter 30N may be formed in a similar manner to the other catheters disclosed herein with the plurality of distinct longitudinally extending convex surfaces 72 positioned circumferentially about longitudinal axis X that collectively define outer surface of the tubular body 256. Unlike the previous embodiments, catheter 30N does not have an enlarged head, but is rather uniform in diameter from the first end to the second end. As will be described in greater detail below, catheter 30N has an entrance opening 208 defined by rounded end wall 220 and rounded transition wall 222 narrowing inwardly towards the longitudinal center axis X towards plane 221 where the inner surface meets with the smooth cylindrical inner surface of the first section 210A of inner surface 210. The rounded end wall 220 flares arcuately in a convex manner outwardly away from the apex of the rounded curve. The outwardly convex flared flat wall 258 meets the upper section 260 of the cylindrical outer surface 256 closely adjacent first end 200. The longitudinal distance where the convexly flared outer surface of rounded end wall 220 meets cylindrical outer surface 260 is located towards the first end relative to end plane 221. Stated otherwise, catheter 30N has asymmetric wall extending in a parabolic shape from the outer convex wall 258 across the apex of the rounded end wall 220 and inwardly into the lumen 202 along the rounded transition wall 222. However, the rounded transition wall 222 extends longitudinally towards the second end a distance farther than the outer rounded flared wall 258. Moreover, rounding of the entrance opening 208 enables the generally cylindrical sidewall of the tubular body to extend closely adjacent the rounded end wall 220, but the cylindrical first section 210A of inner surface 210 does not extend close to the first end as the outer surface.

As depicted in FIG. 34, a catheter 30P in accordance with the present disclosure may have a cylindrical outer surface 256 similar to that of catheter 30N, but have an entrance opening 208 with an elongated convex transition wall 240 terminating at end plane 246 similar to that of catheter 30K. Other features of the first section 210A and second section 210C of inner surface 210 similar with respect those previously described with similar reference numerals and are not repeated herein for brevity, however, to be understood that similar features and characteristics equally apply.

Figure 34A:
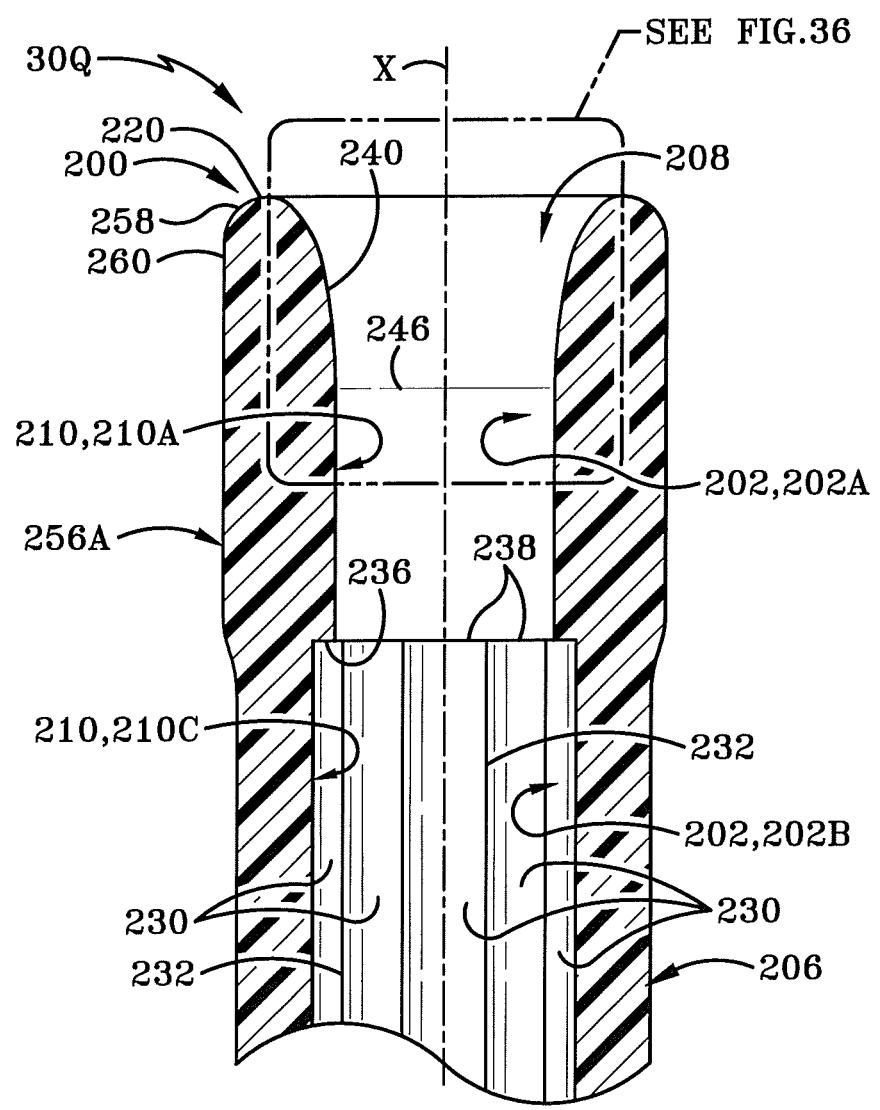
FIG. 34A is an enlarged cross-section view of the first end of a sixteenth embodiment catheter.

As depicted in FIG. 34A, a catheter 30Q in accordance with the present disclosure may have an enlarged cylindrical outer surface 256A operatively defining an enlarged head having a diameter greater than that of the tubular body 206. The enlarged cylindrical outer surface 256A may extend longitudinally from convex wall 258 towards the second end of catheter 30Q. The enlarged cylindrical outer surface 256A taperedly transitions to flush with the tubular body 206 longitudinally proximate the top 238 of the channels 230. In one particularly embodiment, the diameter of the enlarged cylindrical outer surface 256A is one or two French sizes larger than the diameter of the tubular body 206. For example, if the tubular body 206 is a French size 6, then the enlarged cylindrical outer surface 256A is a French size 8. If the tubular body 206 is a French size 8, then the enlarged cylindrical outer surface 256A is a French size 10. If the tubular body 206 is a French size 10, then the enlarged cylindrical outer surface 256A is a French size 12. If the tubular body 206 is a French size 12, then the enlarged cylindrical outer surface 256A is a French size 14. If the tubular body 206 is a French size 14, then the enlarged cylindrical outer surface 256A is a French size 16, and so on. Other features of catheter 30Q with similar reference numerals to those previously described are not repeated herein for brevity, however, are to be understood that similar features and characteristics equally apply to elements identified with similar reference numerals.

Figure 35:
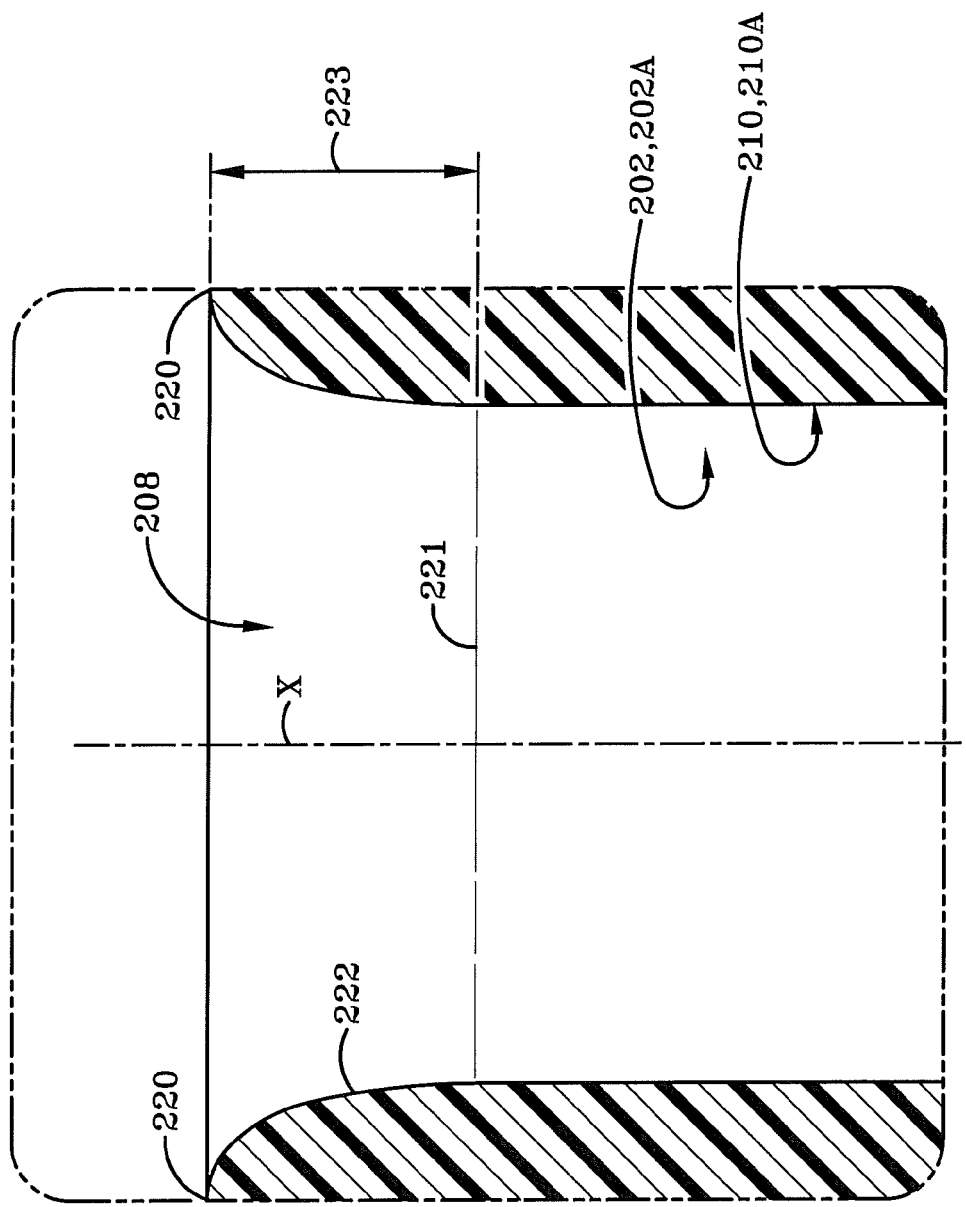
FIG. 35 is an enlarged cross-section view of the box labeled "SEE FIG. 35" in FIG. 27, FIG. 31 and FIG. 33.
Figure 36:
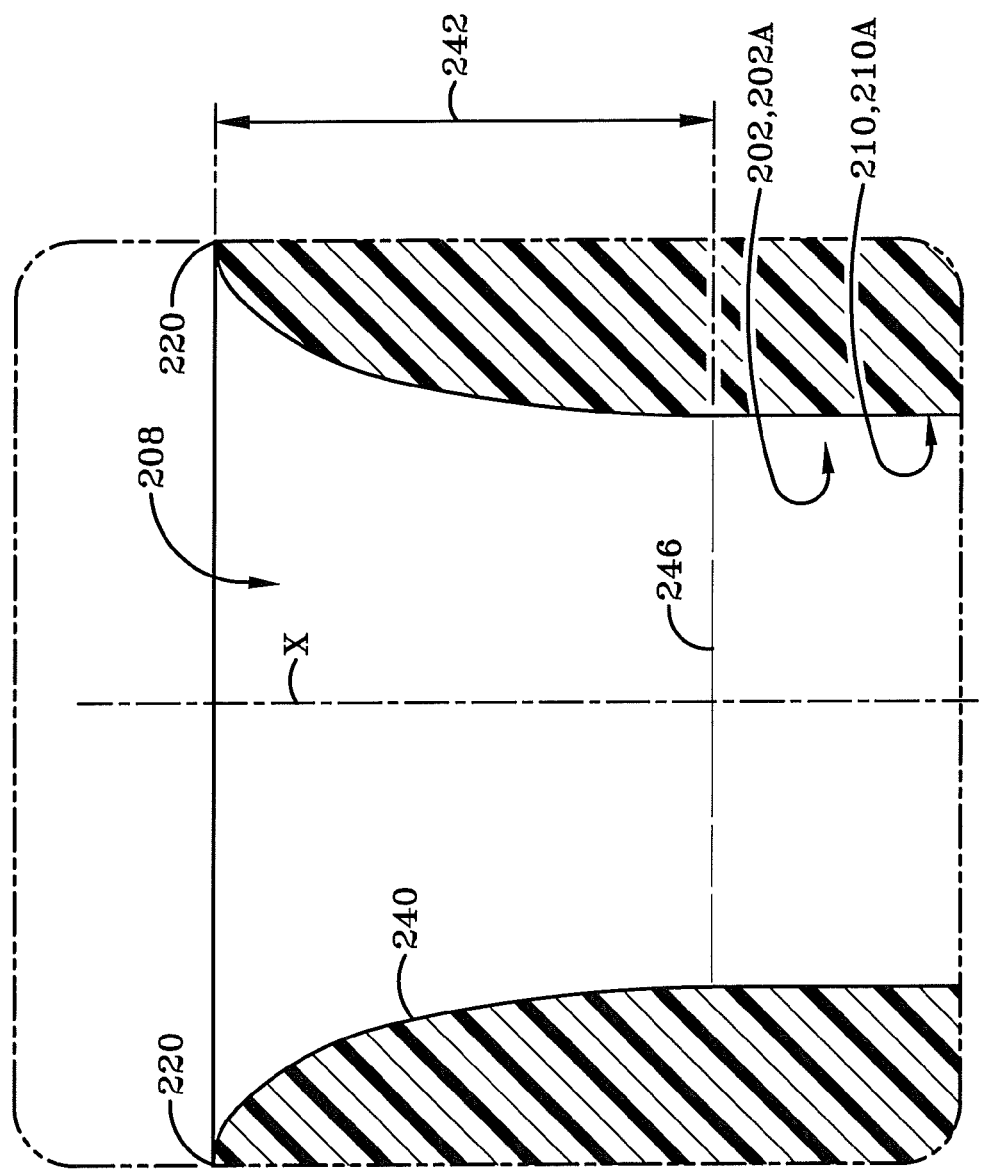
FIG. 36 is an enlarged cross-section view of the box labeled "SEE FIG. 36" in FIG. 29, FIG. 32, and FIG. 34.

FIG. 35 and FIG. 36 are enlarged, detailed cross-sectional views taken from representative entrance openings of various catheters in accordance with the present disclosure. More particularly, FIG. 35 depicts an enlarged cross-section view of the entrance opening and the convex transition wall that defines the opening from catheter 30J in FIG. 27, catheter 30L in FIG. 31, and catheter 30N in FIG. 33. Similarly, FIG. 36 is an enlarged cross-section view detailing the opening and the inner convex transition wall detailing defining the opening of catheter 30K in FIG. 29, catheter 30M in FIG. 32, and catheter 30P in FIG. 34. It is to be understood that the entrance openings defined by the transition walls of any of these catheters may be mixed and matched such as to apply to another catheter in accordance with the present disclosure. The shown detailing is a mere exemplary aspect and may be applied equally to other catheters. For example, the enlarged detail of the opening depicted in FIG. 35 could also be applied and formed in the catheter depicted in FIG. 27, the catheter depicted in FIG. 31, or the catheter depicted in FIG. 33. Likewise, the entrance opening depicted in more detail in FIG. 36 could equally be applied and formed in the catheter of FIG. 27, the catheter of FIG. 31, and the catheter of FIG. 33.

FIG. 35 depicts in more detail the entrance opening 208 formed from the smooth convex transitioning wall 222 extending inwardly towards longitudinal axis X from the rounded end wall 220 and terminating at the end plane 221 before transitioning into the smooth cylindrical surface first section 210A of inner surface 210 that is circular in cross-section. Longitudinal length 223 associated with entrance opening 208 in FIG. 35 varies depending upon the overall French size diameter of the tubular body 206. The transition wall 222 forms a convex parabolic curve that changes from a generally orthogonal direction at the rounded end wall 220 apex to a generally longitudinal direction where the transition wall 222 ceases to continue in an arcuate manner and seamlessly merges at end plane 221 with first section 210A of inner surface 210. Based on the forgoing, the radius relative to the longitudinal axis of the opening 208 is greatest at first end 200. The radius decreases as the rounded transition surface 222 extends towards the second end along the longitudinal axis. At the end plane 221, the radius associated with the transition wall 222 is equal to that of the smooth inner surface first section 210A. While not intending to be limiting, a general shape, when viewed in cross-section, of the transition wall 222 is generally described as if the axis of symmetry associated with the parabolic transition wall 222 extends longitudinally through the apex of the rounded end wall 220. The apex would also equate to the vertex associated with the parabolically curved transition wall 222.

The end plane 221 associated with opening 208 of catheters 30J, 30L, and 30N is offset from the starting point of the channels associated with the second section 210B of inner surface. The distance between end plane 221 and where the channels begin is the length of the first section 210A. The length of first section 210A varies depending upon the French size of the catheter. However, in most instances, it will be in a range from about 0.1 inches to about 2 inches. In other embodiments, the longitudinal length associated with first section 210A of inner surface 210 intermediate the end of the inner channels and end plane 221 is in a range from about 0.1 inches to about 1 inch and in other embodiments, the length associated with first section 210A is about ½ inch.

FIG. 36 depicts the rounded transition wall 240 associated with the opening 208 of catheters 30K in FIG. 29, catheter 30M in FIG. 32, and catheter 30P in FIG. 34. The transition wall 240 extends further into the lumen 202 towards longitudinal axis X such that the tubular body associated near the first end thicker than that of the catheters having a shorter transition wall 222. The longer transition wall 240 extends downwardly to the end plane 246 which equates to a longitudinal distance 242 from the first end 200. Longitudinal distance 242 is greater than that of longitudinal distance 223 and in one particular embodiment, the longitudinal distance 242 may be in a range from about 0.1 inch to 1 inch. The parabolically shaped convex arcuate transition surface 242 extends towards the second end in a narrowing manner such that the radius near end plane 246 is less than that of the radius near the first end 200. The apex of the rounded end wall 220 defines the vertex associated with the parabolically shaped transition wall 240. Since the longitudinal length 242 associated with transition wall 240 is longer than that of transitional wall 222, the first section 210A of inner surface 210 having a smooth cylindrical surface profile is shorter than that which is detailed in FIG. 36. In these embodiments, the longitudinal length associated with first section 210A may be in a range from about 0.05 inch to about 1 inch. The rounded transition wall 240 extends in a convexly arcuate manner from the rounded end wall narrowing inwardly towards the longitudinal axis X and terminates approximately on a similar orthogonal plane as an apex 244 of the enlarged head 204.

Figure 37:
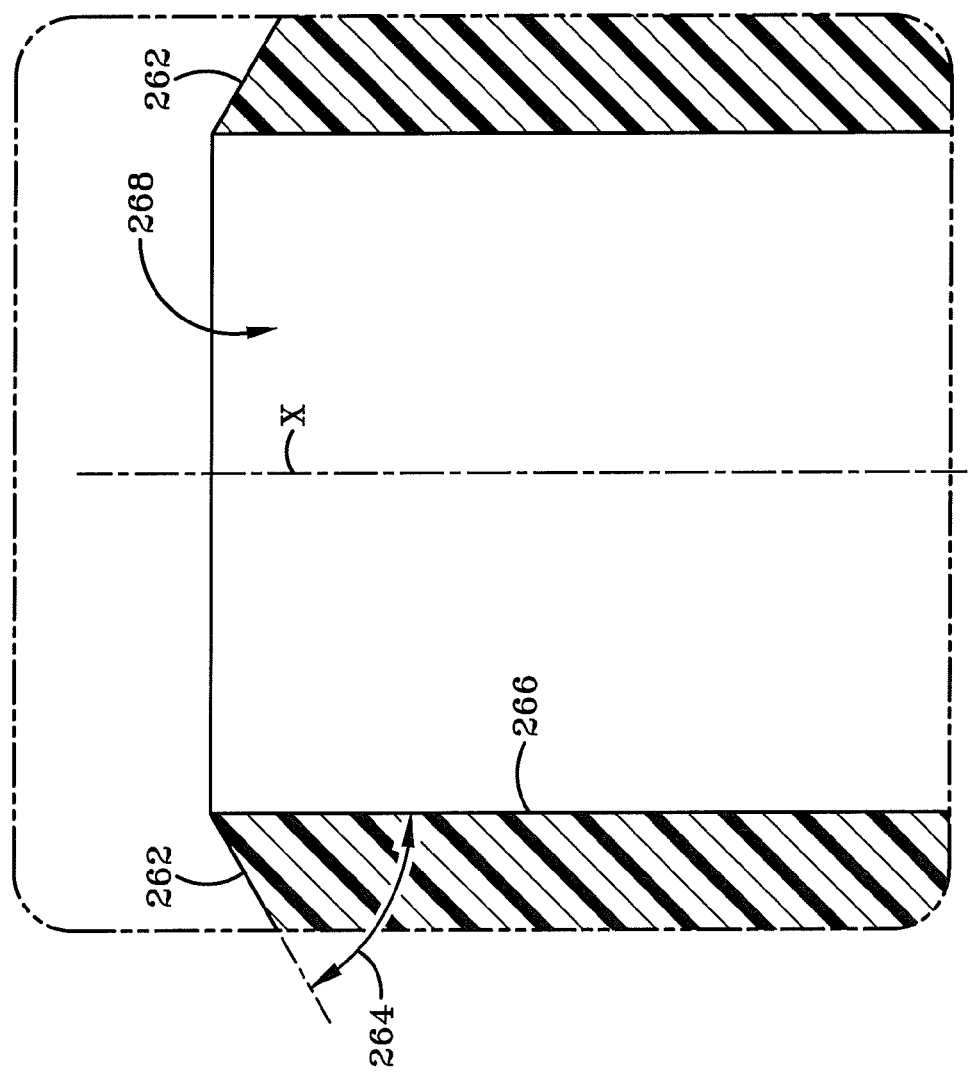
FIG. 37 is an enlarged cross-section view of an alternative embodiment of a catheter opening.

FIG. 37 depicts a catheter in which the entrance opening to the lumen is defined without a tapered opening. In this instance, the inner cylindrical surface the catheter extends to the end of the catheter is uniform relative to longitudinal axis X near its first end. In the embodiment of FIG. 37, an outer wall 262 of the catheter slopes downwardly in an angled or beveled manner such that an acute angle 264 is formed between the beveled surface 262 and the inner surface 266 near the end opening 268.

Figure 38:
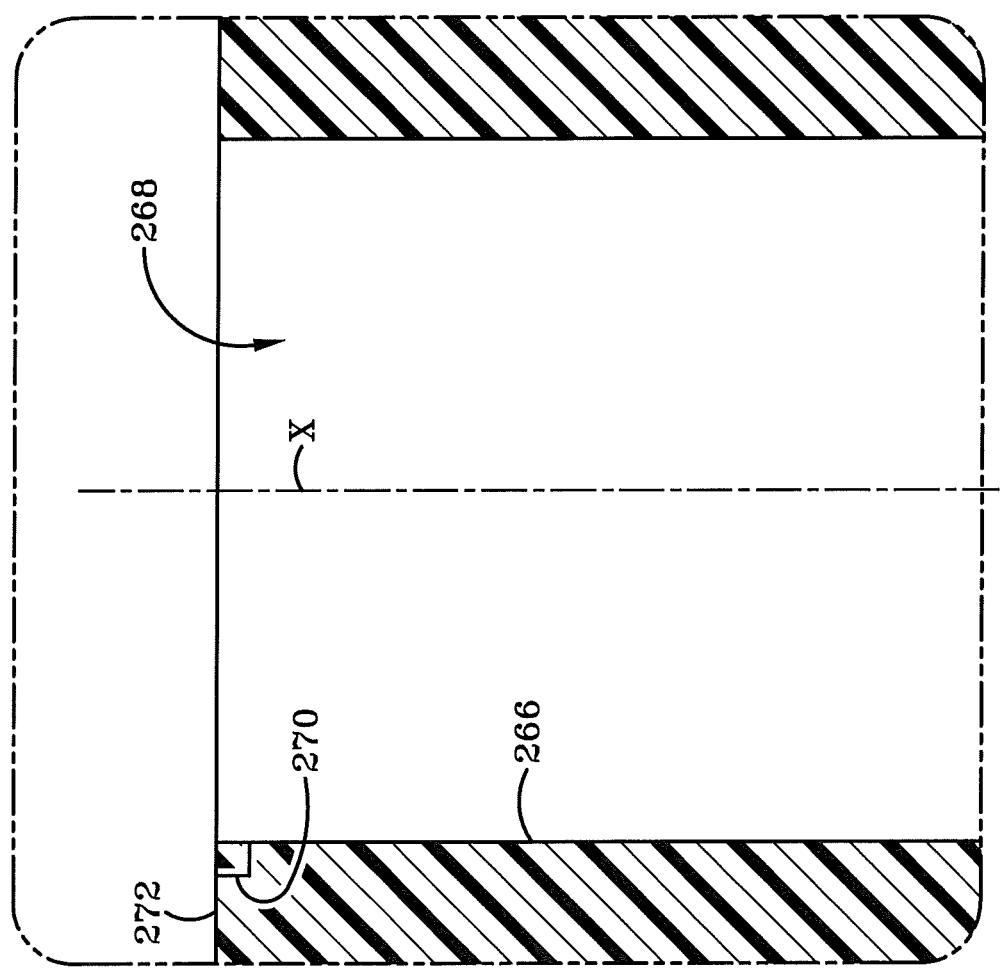
FIG. 38 is an enlarged cross-section view of an alternative embodiment of a catheter opening at the first end.

FIG. 38 depicts an alternative embodiment of the cross-section of an end opening to the longitudinal axis of a catheter wherein the opening 268 is defined by a right angle 270 extending between a flat wall 272 and the inner cylindrical wall 266 of the catheter.

In operation, as seen in FIG. 2, the device of the present disclosure provides a method of draining urine 72 from a human bladder 71. First end 32 of catheter sidewall 36 is first inserted into a urethral canal 70 in a human body until the first end 32 breaches a sphincter wall 73, passes the prostate 74, and is placed in fluid communication with the bladder 71. Bladder 71 contents, namely urine 72, begin to flow toward the first end 32. Urine 72 then flows via gravitational forces over tapered annular recesses 46. Surface 46 tapers inwardly and this permits the fluid to increase velocity or flow rate and decrease its pressure as it approaches entrance opening 38. Urine then passes through entrance opening 38 and longitudinally into lumen 44. As fluid flows through entrance opening 38, it contacts the channels 50. Channels 50 decrease surface side wall friction of the fluid 72 as it exits the bladder 71. The channels 50 on the inner sidewall surface 42 may permit fluid 72 to drain faster than a conventional catheter having a smooth inner sidewall side wall 24 as known in the prior art. Fluid exits the lumen 44 through an exit opening (not shown) at the second end 34 of the catheter and to enter a drainage funnel 45. The catheter 30 remains in fluid communication with the bladder until all of the urine or a desired quantity of urine has drained out of the exit opening (not shown) provided at second end 34 of catheter sidewall 36. Once all urine has drained completely, the catheter may be extracted by gripping the second end 34 and extracting the device 30A out of the urethral canal 70.

One advantage of the present disclosure 30 is that it allows all of the urine to drain out of the bladder. Prior art catheters having eyelets 18 in their sidewalls have been known to not fully drain the bladder as a two eyelet design creates a negative pressure inside the bladder not permitting all urine, fluid or debris contents to drain.

Further, the present disclosure offers advantages over prior art catheters 10 in that when a patient is sick, the urine 72 may become clogged with mucous or other debris. The entrance opening 38 of the present disclosure 30 permits mucous and debris to flow readily into lumen 44 and through the catheter without getting clogged or stuck. In prior art catheters 10, clogging problems with the eyelet 18 design are known to occur.

Alternative embodiment 30B of the present disclosure operates by first aligning truncated tear drop head 56 with urethral canal 70, then inserting head 56 into the urethral canal 70. The head 56 outer diameter OD2 is generally equal to or slightly larger than the upstretched diameter of the urethral canal 70. Catheter 30B is manipulated so the truncated tear drop head 56 advances through the urethral canal 70 until it is in communication with the bladder 71. The head 56 operates as a guide to navigate the natural curvature often found in the urethral canal 70 of males.

Alternative embodiment 30C operates by the first end 32 being first inserted into the urethral canal 70. The convex dimple apices 60B contact the urethral canal 70 during insertion. The convex dimples 60 reduce the surface area of the urethral canal 70 actually contacting the catheter 30C. Thus, dimples 60 reduce irritation often associated with inserting a catheter 10 having a smooth outer surface. Further, retention areas 43 retain a lubricant as catheter 30C moves through the urethral canal 70 towards bladder 71. An exemplary lubricant is commercially sold as Surgilube® manufactured by Savage Laboratories® a division Fougera Pharmaceuticals, Incorporated, A Sandoz Company, of Melville, N.Y. The eyelets of prior art catheters 10 have been known to become clogged or partially clogged with lubricant and thus have decreased flow rates. This problem is obviated in the present catheters 30A, 30B, 30C, 30D, 30E, 30F, 30G, 30H, 30I, 30J, 30K, 30L, 30M, 30N, or 30P. Once urine 72 begins to flow, the dimples 62 along the inner surface of catheters 30A, 30B, 30C, 30D, 30E, 30F, 30G, 30H, 30I, 30J, 30K, 30L, 30M, 30N, or 30P may enable the fluid to drain faster than it normally would over a smooth inner surface. Similar to a dimpled golf ball, the concave dimples permit urine 72 to pool up in the concave dimple 62 recesses. This reduces the friction factor of the remaining urine 72 draining through the lumen permitting it to increase the drainage flow rate while simultaneously permitting laminar flow through the center of the lumen.

While catheters 30A, 30B, 30C, 30D, 30E, 30F, 30G, 30H, 30I, 30J, 30K, 30L, 30M, 30N, 30P, or 30Q of the present disclosure provide for a single entrance opening defined in the first end of the annular sidewall, it is to be understood that more than one opening are possible. For example, a cross member can extend across the opening offering more strength and rigidity to the sidewall. This cross member would bisect the entrance opening into two or more openings. It is to be appreciated that these two or more openings would still operate in accordance with the aspects of the present disclosure.

Alternative embodiment 30D by first aligning truncated tear drop head 92 (channeled head) or 100 (smooth head) with urethral canal 70, then inserting head 92 or 100 into the urethral canal 70. The head 92 (channeled head) or 100 (smooth head) outer diameter OD2 is generally equal to or slightly larger than the upstretched diameter of the urethral canal 70. Catheter 30D is manipulated so the truncated tear drop head 92 (channeled head) or 100 (smooth head) advances through the urethral canal 70 until it is in communication with the bladder 71. The head 92 (channeled head) or 100 (smooth head) operates as a guide to navigate the natural curvature often found in the urethral canal 70 of males, but also works equally well for females. Enlarged heads on catheters 30E and 30F operate in a similar guiding manner.

With continued reference to catheter 30D, convex outer surfaces 72, namely their respective apices, contact the urethral canal 70 as catheter 30D is advanced towards the bladder. The apices on convex surfaces 72 having a greater diameter than reduce the amount of outer surface area directly contacting urethral canal 70. Further, lubricant may be retained in channel(s) 90 to assist in the frictionally reduced gliding advancement of catheter 30D.

It is contemplated that catheter sidewall 36 will be made from a polyvinylchloride thermoplastic having additional plasticizers to make the PVC material soft and flexible for in vivo use, as conventionally known in the art. However, other materials known in the art such as latex or silicone-based derivatives may be substituted as well. Further, it is preferable that sidewall of urinary catheters 30A, 30B, 30C, 30D, 30E, 30F, 30G, 30H, 30I, 30J, 30K, 30L, 30M, 30N, 30P, or 30Q will be made wholly of PVC, or otherwise free of a reinforcing member that is a different material. However, there may be instances in which having a reinforced tube, such as a fully encapsulated reinforcing braid, may be advantageous. Further, it is preferable that sidewall 36 is non-porous so that no bacteria can build up in material recesses, permitting devices 30A, 30B, 30C, 30D, 30E, 30F, 30G, 30H, 30I, 30J, 30K, 30L, 30M, 30N, 30P, or 30Q to be cleaned or disinfected and reused.

It will be understood that while the catheters 30A, 30B, 30C, 30D, 30E, 30F, 30G, 30H, 30I, 30J, 30K, 30L, 30M, 30N, 30P, or 30Q have been described herein as being useful for draining a single fluid (i.e. urine) from a patient's bladder during a drainage session, they may also be used in other medical procedures. Catheters 30A, 30B, 30C, 30D, 30E, 30F, 30G, 30H, 30I, 30J, 30K, 30L, 30M, 30N, 30P, or 30Q may also be used to introduce fluids into a patient's body. Consequently, lumen the lumen is able to permit fluid flow out of a patient's body and into a patient's body. It will further be understood that the fluids in question may be liquids or gases.

Figure 22:
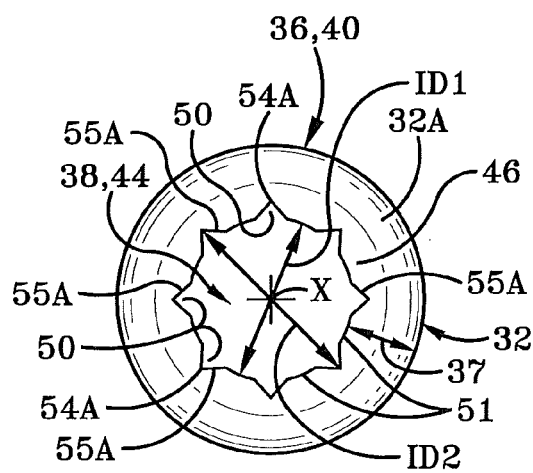
FIG. 22 is a top view of a catheter having an exemplary internal configuration.

As depicted in FIG. 22, an alternative internal configuration of any one of the catheters 30A, 30B, 30C, 30D, 30E, 30F, 30G, 30H, 30I, 30J, 30K, 30L, 30M, 30N, 30P or 30Q, is provided. A portion of lumen 44 is defined by longitudinally extending edge 54A connecting adjacent flat panel walls 55A together. Flat panel walls 55A extend towards longitudinal center axis X from their connection with edge 54A. Flat panel walls 55A contact arcuate wall 51. Arcuate wall 51 has a radius of curvature equal to first inner diameter ID1 divided by two. Furthermore, first inner diameter ID1 is measured from arcuate wall 51 through longitudinal axis X to an opposed arcuate wall 51. A second inner diameter ID2 is measured through longitudinal axis X between opposed longitudinal edges 54A. Second inner diameter ID2 is greater than first inner diameter ID1. Channels 50 are defined between flat panel wall 55A and have a v-shaped configuration in cross section. The advantage of this configuration is designed to improve fluid flow through lumen 44 inside a catheter.

Figure 23:
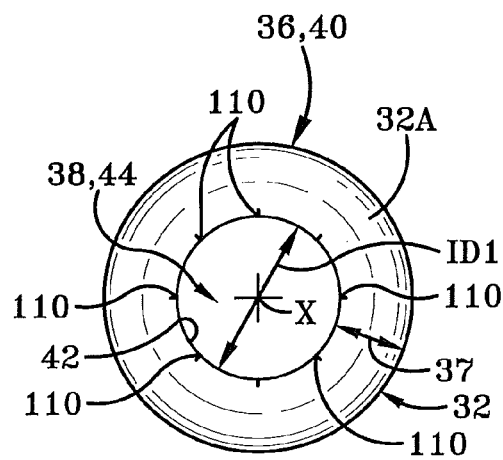
FIG. 23 is a top view of a catheter having another exemplary internal configuration.

As depicted in FIG. 23, the inner surface 42 defining lumen 44 may be scored with a plurality of score lines 110 circumferentially disposed about longitudinal axis X. Score lines 110 extend slightly into the catheter body away from longitudinal axis X. Score lines 110 help to reduce surface tension of fluid moving through lumen 44. In the shown embodiment of FIG. 23, score lines 110 extend longitudinally in a linear manner along the length of the catheter body. However, it is to be clearly understood that the score lines 110 may helically wind about longitudinal axis X creating a rifling effect of the fluid moving through lumen 44 inside the catheter. The score lines 110 are preferably used in association with a catheter having a French size less than about French size 10. However, clearly it is contemplated that larger sizes may be used as well. In one particular example, score lines 110 are provided on a catheter having a French size 4.

In the foregoing description, certain terms have been used for brevity, clearness, and understanding. Namely, the term "non-circular cross section" with reference to the inner or outer surface refers to the annular wall 36 defining the lumen of the catheter not having a continuous circular extending cross section. Specifically, the inner surface is non-circular because it may contain longitudinally extending straight channels, rifled channels, helical channels, textured dimples, staggered recesses, turbulence reducing molding, or other striations that intentionally break the fluid friction or tension which would ordinarily occur against a smooth inner catheter wall. The term "eyeletless" refers to the absence of any eyelet formed in the sidewall of a catheter sidewall as ordinarily understood and used in the prior art; stated otherwise, the term eyeletless refers a catheter annular sidewall that is continuous. The term "dimples" or "dimpled" refers to a plurality of hemispheric recesses formed on a surface. The dimples on the inner surface of the catheter cause a fluid boundary layer entering the lumen from an entrance opening to transition from laminar to turbulent within the hemispheric recess. The turbulent boundary layer within the hemispheric recess is able to remain attached to the inner surface much longer than a purely smooth surface having a laminar boundary and so creates a narrower, low pressure, wake and hence less pressure drag (i.e., friction). The reduction in pressure drag or friction causes the fluid to drain more rapidly.

Again, it is to be clearly understood that the internal geometric configurations of the lumen of any catheter embodiment 30A, 30B, 30C, 30D, 30E, 30F, 30G, 30H, 30I, 30J, 30K, 30L, 30M, 30N, 30P, 30Q can be fabricated with any of the outer geometric configurations of catheter embodiment 30A, 30B, 30C, 30D, 30E, 30F, 30G, 30H, 30I, 30J, 30K, 30L, 30M, 30N, 30P, 30Q. So for example, the internally dimpled lumen presented in FIG. 10C may be used in combination with any catheter embodiment 30A, 30B, 30C, 30D, 30E, 30F, 30G, 30H, 30I, 30J, 30K, 30L, 30M, 30N, 30P, or 30Q. Additionally, the internal lumen configuration including a flat wall presented in FIG. 6A may be used in combination with any catheter embodiment 30A, 30B, 30C, 30D, 30E, 30F, 30G, 30H, 30I, 30J, 30K, 30L, 30M, 30N, 30P, or 30Q.

The term "intermittent" refers to a type of catheter that is not permanent fixture or a repeatably used urine draining device having a balloon seal, such as a Foley-type catheter. Rather, the intermittent catheter 30A, 30B, 30C, 30D, 30E, 30F, 30G, 30H, 30I, 30J, 30K, 30L, 30M, 30N, 30P, or 30Q is configured to be inserted into urethral, drain urine a single time, then be removed and discarded.

It is believed that the catheter the intermittent catheter 30A, 30B, 30C, 30D, 30E, 30F, 30G, 30H, 30I, 30J, 30K, 30L, 30M, 30N, 30P, or 30Q in accordance with the present disclosure may reduce bladder-wall trauma caused by the insertion of the traditional catheters into the bladder. Particularly, the catheters the intermittent catheter 30J, 30K, 30L, 30M, 30N, 30P, or 30Q may help reduce catheter-associated urinary tract infections (CAUTIs). The use of the smooth first section 210A having a smooth circular cross section can protect the mucosal lining of the bladder (which prevents bacteria from adhering to the bladder wall and forming colonies) in the event that the bladder wall is inadvertently sucked into the lumen 202 through the opening. This is advantageous over traditional Foley-type catheter that breaks down this mucosal lining defense in when a traditional eyelet on a Foley-type catheter traumatically contacts the bladder wall and sucking the bladder wall into the eyelet.

No unnecessary limitations are to be implied therefrom beyond the requirement of the prior art because such terms are used for descriptive purposes and are intended to be broadly construed.

Moreover, the description and illustration of the preferred embodiment of the disclosure are an example and the disclosure is not limited to the exact details shown or described.

What is claimed:

1. A urinary catheter comprising:
   a first end opposite a second end defining a longitudinal axis therebetween;
   a tubular body extending from the first end to the second end having an outer surface and an inner surface defining a urine draining lumen adapted for draining urine from a bladder and wherein the urinary catheter can be deployed without a solid structure moving through the lumen when the tubular body is inserted into the bladder;
   a first section of the inner surface proximate the first end that is generally circular in cross section; and
   a second section of the inner surface that is generally non-circular in cross section; wherein the second section is farther from the first end than the first section of the inner surface.

2. The urinary catheter of claim 1, further comprising:
   a plurality of longitudinal channels formed in the second section extending towards the second end from a first plane orthogonal to the longitudinal axis; wherein the first section is located on one side of the first plane opposite the second section located on the other side of the first plane.

3. The urinary catheter of claim 2, wherein the first plane in a range from about 0.1 inches to about 2 inches from the first end of the tubular body.

4. The urinary catheter of claim 1, further comprising:
   a rounded endwall at the first end;
   an arcuately convex transitional surface narrowing inwardly towards the longitudinal axis; wherein the rounded endwall and the arcuately convex transitional surface define an entrance opening to the lumen that is generally orthogonal to the longitudinal axis.

5. The urinary catheter of claim 1, further comprising:
   a fixed enlarged head defining a portion of the outer surface positioned proximate the first end; and
   an arcuately convex transitional wall narrowing inwardly towards the longitudinal axis defining an entrance opening to the lumen.

6. The urinary catheter of claim 5, further comprising:
   an end plane associated with the transitional wall where the transitional wall meets the circular cross-section of the first section of the inner surface;
   wherein the end plane intersects the enlarged head.

7. The urinary catheter of claim 6, wherein the end plane intersects the enlarged head at an apex.

8. The urinary catheter of claim 1, further comprising:
   a plurality of arcuately concave channels defining the second section of the inner surface, wherein the arcuately concave channels are positioned circumferentially around the longitudinal axis.

9. The urinary catheter of claim 8, wherein the plurality of channels is an odd number of channels.

10. The urinary catheter of claim 9, wherein the number of channels is selected from the group consisting of: five channels, seven channels, or nine channels.

11. The urinary catheter of claim 1, further comprising:
    a plurality of distinct longitudinally extending arcuately convex surfaces collectively defining the outer surface of the tubular body.

12. The urinary catheter of claim 1, further comprising:
    a vertically asymmetric parabolically-shaped transitional wall extending inwardly from the first end to the first section of the inner surface.

13. The urinary catheter of claim 1, further comprising:
    a beveled transition between the first section and the second section of the inner surface.

14. The urinary catheter of claim 1, further comprising:
    a point on the non-circular second section of the inner surface having a radius relative to the longitudinal axis that is different than a radius of the first section of the inner surface.

15. A catheter comprising:
    a first end opposite a second end defining a longitudinal axis therebetween;
    a tubular body extending from the first end to the second end having an outer surface and an inner surface defining a lumen adapted to drain fluid from body cavity;
    a non-expandable enlarged head forming a portion of the outer surface proximate the first end, and the enlarged head having a diameter greater than the tubular body;
    a rounded endwall at the first end; and
    an arcuately convex transitional wall seamlessly narrowing from the rounded endwall to the inner surface of the tubular body, wherein the rounded endwall and the arcuately convex transitional wall define an opening generally orthogonal to the longitudinal axis;
    wherein the catheter can be deployed without a solid structure moving through the lumen.

16. The catheter of claim 15, wherein the rounded endwall and the arcuately convex transitional wall are vertically asymmetric.

17. The catheter of claim 15, wherein the arcuately convex transitional wall decreases in diameter from the first end towards the second end; and wherein the enlarged head increases in diameter from the first end towards an apex of maximum diameter and then decreases in diameter from the apex towards the second end.

18. The catheter of claim 15, further comprising:
a plurality of arcuately convex surfaces collectively defining the outer surface of the tubular body;
a plurality of arcuately concave surfaces collectively defining a portion of the inner surface of the tubular body.

19. The catheter of claim 18, further comprising:
a first section of the inner surface having a circular cross section; and
a second section of the inner surface having a non-circular cross-section defined by the plurality of arcuately concave surfaces.

20. The catheter of claim 15, further comprising:
a beveled transition wall intermediate the first section and the second section of the inner surface.

21. A catheter comprising:
a tubular body member defining a lumen extending centrally along a longitudinal axis from a first end to a second end and the tubular body having an endwall connected with an inwardly rounded conical section seamlessly tapering towards the longitudinal axis defining an entrance opening to the lumen that is generally orthogonal to the longitudinal axis;
an inner surface spaced apart from an outer surface of the tubular member, wherein the inner surface defines the lumen adapted to drain fluid; and
a plurality of distinct longitudinally extending arcuately concave channels positioned circumferentially about the longitudinal axis collectively defining the inner surface;
wherein the catheter can be deployed without a solid structure moving through the lumen.

* * * * *